United States Patent [19]

Seymour et al.

[11] Patent Number: 4,923,454

[45] Date of Patent: * May 8, 1990

[54] MICROFIBER-CONTAINING ABSORBENT STRUCTURES AND ABSORBENT ARTICLES

[75] Inventors: Mark D. Seymour; Michael F. LiCause; Thomas H. Daugherty, all of Cincinnati, Ohio

[73] Assignee: The Procter & Gamble Company, Cincinnati, Ohio

[*] Notice: The portion of the term of this patent subsequent to Sep. 27, 2005 has been disclaimed.

[21] Appl. No.: 146,004

[22] Filed: Jan. 20, 1988

[51] Int. Cl.$^5$ .............................................. A61F 13/16
[52] U.S. Cl. .................................... 604/368; 684/371
[58] Field of Search ............... 604/364, 365, 366, 367, 604/368, 369, 370, 371, 374, 378, 381, 382, 358; 428/171, 172, 221, 224, 225, 283, 281, 286, 282, 288, 289; 528/432

[56] References Cited

U.S. PATENT DOCUMENTS

| | | | |
|---|---|---|---|
| 3,016,599 | 1/1962 | Perry | 428/338 |
| 3,594,266 | 7/1971 | Okazaki et al. | 161/173 |
| 4,100,324 | 7/1978 | Anderson et al. | 428/288 |
| 4,103,058 | 7/1978 | Humlicek | 428/171 |
| 4,113,794 | 9/1978 | Thompson et al. | 260/857 TW |
| 4,130,602 | 12/1978 | Thompson | 525/432 |
| 4,136,133 | 1/1979 | Thompson | 525/432 |
| 4,168,602 | 9/1979 | Thompson | 525/432 |
| 4,429,001 | 1/1984 | Kolpin et al. | 428/283 |
| 4,584,053 | 7/1984 | Lofquist et al. | 525/183 |
| 4,468,428 | 8/1984 | Early et al. | 428/221 |
| 4,558,097 | 12/1985 | Lofquist et al. | 525/183 |
| 4,620,479 | 3/1987 | Insley | 604/358 |
| 4,673,402 | 6/1987 | Weisman et al. | 604/368 |
| 4,724,184 | 2/1988 | Killian et al. | 428/227 |
| 4,773,903 | 9/1988 | Weisman et al. | 604/378 |
| 4,784,892 | 11/1988 | Storey et al. | 428/172 |

FOREIGN PATENT DOCUMENTS

| | | |
|---|---|---|
| 1074475 | 3/1980 | Canada . |
| 156649 | 10/1985 | European Pat. Off. . |
| 1271763 | 9/1960 | France . |
| 57-121620 | 7/1982 | Japan . |
| 2113731A | 8/1983 | United Kingdom . |
| WO84/03833 | 10/1984 | World Int. Prop. O. . |

OTHER PUBLICATIONS

"Hydrophilic Nylon for Improved Apparel Comfort", Textile Research Journal, 7/85 pp. 325–333, Lofquist et al.,
"Impact-87 Conference Coverage-Pat 1", Nonwovens World, vol. 2, No. 2, May–Jun. 1987, p. 85–56.
"Permanently Hydrophilic Synthetic Fabrics", Nowwovens World, May.–Jun. 1986, pp. 113–115, McDevitt et al.

Primary Examiner—Max Hindenburg
Assistant Examiner—K. M. Reiche
Attorney, Agent, or Firm—George W. Allen; Jerry J. Yetter; Richard C. Witte

[57] ABSTRACT

The present invention relates to absorbent web structures suitable for incorporation into absorbent articles such as sanitary napkins, diapers, incontinent devices, training pants and the like. Such structures comprised webs of entangled melt blown microfibers which are prepared from a particular type of hydrophilic nylon copolymer. Preferred hydrophilic cylon microfiber-based webs also contain staple fibers and/or particles of hydrogel-forming polymeric gelling agent. Web structures containing hydrophilic nylon microfibers have specially desirable comfort, integrity and fluid handling characteristics.

17 Claims, 2 Drawing Sheets

MICROFIBER-CONTAINING ABSORBENT STRUCTURES AND ABSORBENT ARTICLES

BACKGROUND OF THE INVENTION

The present invention relates to microfiber-based web structures suitable for absorbing discharged body fluids. Such structures can be incorporated into disposable absorbent articles such as sanitary napkins, infant diapers, adult incontinence pads and the like.

Absorbent structures which comprise entangled masses of fibers, i.e., fibrous webs, are well known in the art. Such structures can imbibe liquids, such as discharged body fluids, both by an absorption mechanism wherein fluid is taken up by the fiber material itself and by a wicking mechanism wherein fluid can be acquired by, distributed through and stored in the capillary interstices between fibers.

While absorbent capacity is a significant factor in determining the suitability of absorbent structures for use in disposable absorbent articles, other factors can also be important. For disposable absorbent articles which are worn or positioned in a particular relationship to the user's body, mechanical properties of the absorbent structures utilized in such articles are likewise relevant considerations. Thus features such as flexibility; resilience, e.g. resistance to bunching; softness; and tear resistance, e.g. strength and integrity, must generally be taken into account when selecting appropriate types of absorbent structures for use in absorbent articles. Absorbent structure properties which determine the comfort of the absorbent articles incorporating such structures are especially important in products like sanitary napkins and adult incontinence pads wherein the intimate contact of the article with the wearer's body make the comfort properties of such structures especially noticeable.

One way of imparting strength, flexibility and wet integrity to fibrous web absorbent structures has involved the use of blown microfibers in combination with staple absorbent fibers to fashion absorbent products. Anderson et al, U.S. Pat. No. 4,100,324; issued July 11, 1978, for example, discloses preparation of absorbent "fabrics" fashioned from blown microfibers and wood pulp fibers. Technology has also been developed to enhance the absorbent capacity of microfiber/staple fiber webs by incorporating therein particles of fluid-absorbent polymeric materials. For example, Kolpin/Brownlee, U.S. Pat. No. 4,429,001, issued Jan. 31, 1984, discloses sorbent sheet materials which comprise webs of entangled blown microfibers, generally absorbent staple fibers and particles of solid, high-sorbency, liquid-sorbent polymer materials.

Microfiber-based absorbent web structures of the prior art can utilize a wide variety of polymeric materials to form the microfiber component thereof. Frequently, however, the microfiber materials which provide webs with the most desirable strength, integrity, flexibility and resilience characteristics are also materials which are in and of themselves relatively hydrophobic polymers such as polyolefins, polyesters or other nonwettable polymeric materials. Absorbent webs containing such relatively hydrophobic polymeric, e.g. polypropylene, microfibers thus can be relatively poor at acquiring and distributing liquids within their structure unless steps are taken to improve the fluid handling propensity of such webs.

One technique frequently employed to improve the fluid handling characteristics of microfiber-based absorbent webs is to incorporate additional fibrous or nonfibrous particulate components into such webs as fluid distribution aids. Thus, for example, Insley; U.S. Pat. No. 4,650,479; issued Mar. 17, 1987, discloses the preparation of microfiber-based absorbent sheet products employing liquid transport fibers therein. Furthermore, both Kimberly-Clark Limited; British Patent Specification No. 2,113,731A; published Aug. 10, 1983 and the co-pending application of Weisman and Daugherty having U.S. Ser. No. 091,805; filed Sept. 1, 1987, disclose incorporation of certain kinds of non-fibrous particulate material into microfiber-based absorbent web structures in order to enhance fluid acquisition by and fluid distribution throughout such structures.

Perhaps the most common technique for enhancing the fluid acquisition characteristics of microfiber-based absorbent web structures is to incorporate a hydrophilizing agent within or onto those web components which would otherwise be unacceptably hydrophobic in nature. Common hydrophilizing agents include surfactants and/or silica, and these agents are frequently added to the microfiber-based web or web components at any suitable time before, during or after web preparation. The aforementioned Kolpin/Brownlee, Insley, Kimberly-Clark Limited and Weisman/Daugherty patent references all disclose the utilization of a hydrophilizing agent to improve the fluid handling characteristics of microfiber-based absorbent webs.

When liquid transport fibers, fluid distribution particles or hydrophilizing agents are employed, the addition of any or all of these components to microfiber-based absorbent webs tends to increase both the cost and processing complexity of preparing such structures. Furthermore, when hydrophilizing agent is incorporated in or on the relatively hydrophobic components of microfiber-based webs, the hydrophilizing effect of this treatment is generally not permanent. Prolonged contact of the hydrophilized components with aqueous fluids can cause the hydrophilizing agent to be washed away from portions of the web structure and potentially reduce fluid surface tension, such that the overall fluid management characteristics of the structure may diminish over time.

Given the foregoing considerations, there is a continuing need to identify microfiber-based absorbent web structures which provide the usual desirable strength, integrity, flexibility and resilience characteristics inherent in such structures but which also provide acceptable fluid handling and fluid management characteristics. Accordingly, it is an object of the present invention to provide improved absorbent web structures containing a particular type of hydrophilic melt blown microfibers which are especially effective at acquiring and handling the aqueous liquids such as body fluids which such structures are to imbibe.

It is a further object of the present invention to provide such microfiber-based absorbent web structures which exhibit these desirable fluid handling and fluid management characteristics without using, or with reduced use of, conventional fluid distribution aids such as transport fibers, particulate additives and/or hydrophilizing agents.

It is a further object of the present invention to provide such improved fluid handling, microfiber-based absorbent structures which retain the usual benefits afforded by microfibers in absorbent webs including desirable integrity, wet strength, flexibility and resilience characteristics.

It is a further object of the present invention to provide at reasonable cost disposable absorbent articles such as sanitary napkins, diapers, training pants, incontinence products and the like which utilize such improved microfiber-based absorbent web structures to form their absorbent cores.

SUMMARY OF THE INVENTION

The present invention is directed to a particular type of absorbent web structure which is especially effective for acquiring and distributing aqueous fluids throughout such a structure. Such a structure comprises an entangled web of melt-blown microfibers having diameters which range from about 0.5 to 60 microns. The melt blown microfibers are furthermore formed from a particular type of thermoplastic copolymer which comprises both a nylon component and a hydrophilizing polymeric component. The hydrophilizing polymeric component of this copolymer is one which renders the resulting copolymer hydrophilic and which provides a copolymer which has a melting point of from about 100° C. to 265° C. and a melt viscosity of from about 1 to 400 Pa-s.

Web structures comprising microfibers fashioned from hydrophilic nylon copolymers of the foregoing characteristics have a dry density which ranges from about 0.006 to 0.3 g/cm$^3$. Preferred web structures of this type having especially desirable flexibility and resilience characteristics and especially desirable fluid absorbency characteristics can optionally also comprise from about 10% to 90% by weight of substantially nonabsorbent synthetic staple fibers and/or from about 5% to 60% by weight of particles of a polymeric gelling agent.

The present invention is also directed to absorbent articles such as sanitary napkins, infant diapers, training pants, adult incontinence products and the like which utilize the absorbent web structures herein in their absorbent cores. Such articles comprise a liquid impervious backing sheet, a liquid pervious top sheet and the web structure-containing absorbent core positioned between the backing sheet and the topsheet.

DETAILED DESCRIPTION OF THE INVENTION

Figure 1:
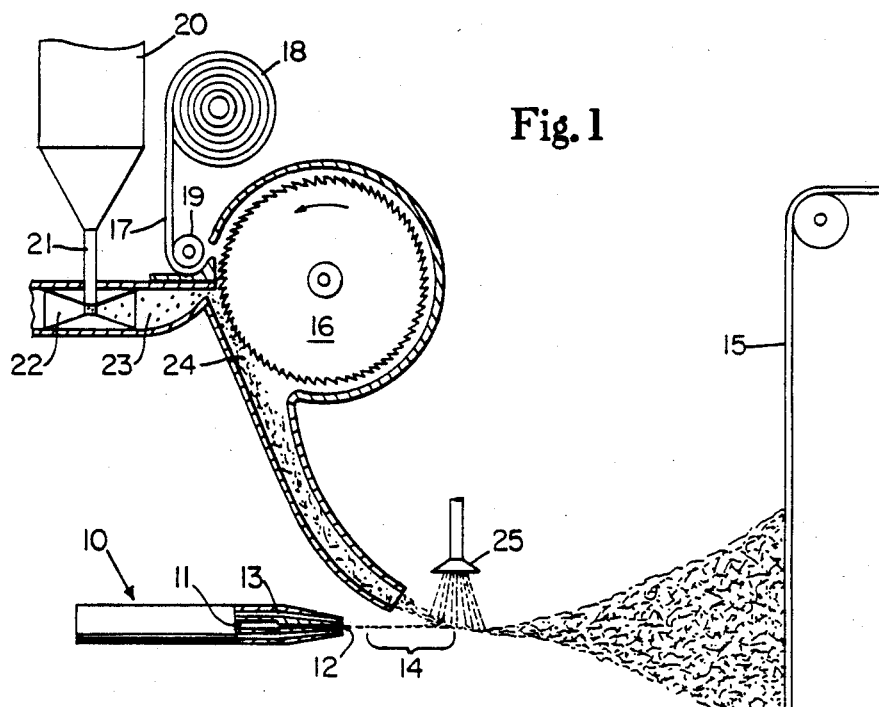
FIG. 1 is a schematic diagram of apparatus used in preparing preferred composite absorbent structures of this invention.

The absorbent structures of the present invention are webs which, in their preferred embodiments, can contain both fibrous and nonfibrous components. For purposes of this invention, the terms "fibers" and "fibrous" refer to a specific type of "particulate" material wherein the length to diameter ratio of such particulate material is greater than about 10. "Nonfibrous" particles, conversely, are those wherein the length to diameter ratio is about 10 or less.

The essential component of the absorbent web structures herein comprises melt blown microfibers formed from a hydrophilic nylon copolymer material that provides fibers of particular size, strength and hydrophilicity characteristics. Such melt blown microfibers are very fine fibers prepared by extruding liquefied, i.e. melted, fiber-forming copolymer through orifices in a die into a high velocity gaseous stream. Fibers are attenuated by the gaseous stream and are subsequently solidified. The resulting stream of solidified fibers can be collected, e.g. on a screen disposed in the gaseous stream, as an entangled coherent fibrous mass. Such an entangled fibrous mass is characterized by extreme entanglement of the microfibers. This entanglement provides coherency and strength to the resulting web structure. Such entanglement also adapts the web structure to contain the optional staple fiber and particulate components, e.g. polymeric gelling agents, within the structure if such optional components are utilized. The microfibers are entangled sufficiently that it is generally impossible to remove one complete microfiber from the mass of microfibers or to trace one microfiber from beginning to end. The theoretical aspect ratio (ratio of length to diameter) of blown microfibers in the web structures herein approaches infinity, although significant discontinuity of the microfibers can occur during web preparation.

The melt blown microfibers which form the essential component of the absorbent web structures herein must be of a certain size in order to impart the requisite flexibility, integrity and resilience features to such absorbent structures. In particular, substantially all of the individual melt blown microfibers included in the structures herein should have a diameter ranging from about 0.5 to 60 microns. More preferably the microfibers will have an average diameter ranging from about 1 to 30 microns. Most preferably, microfiber diameter will range from about 1 to 10 microns.

The microfibers utilized will frequently be generally cylindrical in shape but other fiber geometries are also possible, e.g. wherein cross-sections of the microfibers are elliptical, rectangular, triangular, etc. For purposes of the present invention, microfiber diameter can be determined from microfiber cross-sectional area, calculated by assuming that such cross-sectional area is circular.

In order to impart the requisite fluid handling properties to the absorbent structures herein, the melt blown microfibers which form a part, if not all, of the absorbent web structure must be fashioned from a particular type of thermoplastic, hydrophilic nylon copolymer. By preparing the structures of this invention from hydrophilic nylon microfibers, these structures retain the desirable strength, flexibility and resiliency characteristics of conventional, e.g. polypropylene-based, microfiber webs, but such structures are far superior to conventional microfiber webs in their tendency to acquire and transport aqueous fluids within and throughout the structure. Such desirable fluid handling characteristics can further be realized without treating the web microfibers with surfactant or other hydrophilizing agents as is conventionally done when relatively hydrophobic materials such as polypropylene are used to form microfiber-based absorbent webs.

One essential component of the thermoplastic copolymer used to form the microfibers of the structures herein comprises a conventional nylon polymer chain. Nylon polymers are polyamides which can be obtained, for example, by the condensation polymerization reaction of a polyacid and a polyamine. Depending upon the nature of the reactants employed, various forms of nylon can be utilized as the nylon component of the copolymers herein. Examples of these various forms of nylon include nylon-6,6 [also known as poly(hexamethylene adipamide)]; nylon-6,10 [poly(hexamethylene sebacamide)]; nylon-6 [poly(pentamethylene carbonamide)]; nylon-11 [poly(decamethylene carbonamide)]; MXD-6 [poly(meta-xylene adipamide)]; PACM-9 [bis(para-aminocyclohexyl)methane azelamide]; PACM-10 [bis(para-aminocyclohexyl)-methane sebacamide] and PACM-12 [bis(para-aminocyclohexyl)methane dodecanoamide]. Methods for preparing these nylon-type polyamides are well known and described in numerous patents and trade journals. Of all of the foregoing nylon materials, the most preferred is nylon-6 which can be prepared by the polymerization of caprolactam.

To provide the thermoplastic copolymer used to form the microfibers of the absorbent structures herein, nylon polymer chains or materials which form such chains as hereinbefore described, are copolymerized with a particular type of hydrophilizing polymeric entity. Such a hydrophilizing polymeric entity is one which renders the resulting copolymer hydrophilic and which also imparts certain other physical characteristics to the resulting modified nylon copolymers. For purposes of the present invention, a fiber-forming, nylon-based copolymer is considered to be hydrophilic if water or aqueous body fluid readily spreads on or over the surface of a solid mass of such a copolymer (e.g. the copolymer in the form of a fiber, chip, block, sheet, etc.). The degree of hydrophilicity of such copolymers can be quantified by referencing the advancing contact angle between a drop of water and the horizontal surface of a solid mass of the copolymer.

The contact angle concept is well-known. In general, advancing contact angle can be defined for purposes of this invention as the angle between the surface of the copolymer mass and the vector which is tangent to a water drop at the point of its contact with the copolymer surface, i.e. at the point of the interline between the drop and the surface. Contact angle is generally measured in the liquid phase as the interline advances over the copolymer surface and, for purposes of this invention, is determined at a temperature of 20° C. and relative humidity of 65%. Determination of advancing contact angle between water and a mass of the hydrophilic nylon copolymer can be made in the general manner described in Adamson, A. W., *Physical Chemistry of Surfaces,* Wiley-Interscience, 3rd Ed., 1976, or in Daugherty, T. H., "Dynamic Wetting of Single Pulp Fibers, MS Thesis, University of Washington, 1981, both of which publications are incorporated herein by reference. Preferably the hydrophilic nylon copolymer used to form microfibers of the absorbent structures herein will have an advancing contact angle with water of 90° or less, more preferably such a copolymer will have an advancing contact angle with water between about 0° and 60°.

One property of the hydrophilic nylon copolymers useful herein which can affect the hydrophilicity of such copolymers is the propensity of such materials to absorb moisture. Moisture absorption by the hydrophilic nylon microfibers can actually alter the hydrophilicity characteristics of the fiber surfaces. Moisture absorption by the hydrophilic nylon microfibers used in the structures of this invention also tends to improve the comfort properties of such structures by helping to impart "breathability" to articles containing such structures. The moisture absorption characteristics of the hydrophilic nylon material used in the structures herein can be determined either by measuring the amount of water absorbed as a percentage of the initial dry weight of the material after conditioning for a time period within a controlled temperature and relative humidity environment, or by measuring the water retention value (WRV) of the fibers after they are contacted with liquid water.

In addition to its hydrophilic surface characteristics, the nylon-based copolymer used to form the microfibers of the structures herein must also have certain melting point and melt viscosity characteristics. In particular, the microfibers essentially utilized in the structures herein are formed from a hydrophilic nylon copolymer which has a melting point which is below the temperature at which the copolymer decomposes, i.e. below the point at which there is a change in the chemical nature of the monomer units present in the copolymer structure. Thus in general the hydrophilic nylon copolymers useful herein will have a melting point of from about 100° C. to 265° C., more preferably from about 200° C. to 250° C., most preferably from about 218° C. to 228° C. For purposes of this invention, melting point is determined by differential scanning calorimetry.

Furthermore, the hydrophilic nylon copolymer used to form the essential microfiber component of the structures herein will also generally have certain melt viscosity characteristics. Melt viscosity should be determined for the hydrophilic nylon copolymer material under those conditions which are encountered when such a copolymer is melt blown into fibers using a heated fiber-forming die apparatus as hereinafter more fully described. For purposes of this invention, these conditions include a molten copolymer temperature of 260° C. to 265° C. and copolymer shear rate of 2,000 sec$^{-1}$. Under these conditions, the hydrophilic nylon copolymer should generally have a melt viscosity of from about 1 to 400 Pa-s, more preferably from about 10 to 150 Pa-s, most preferably from about 30 to 130 Pa-s. Melt viscosity can be determined using a capillary melt rheometer using a 33 to 1 orifice.

The microfiber-forming hydrophilic nylon copolymer may be either a block or a graft copolymer formed from its respective nylon and hydrophilizing polymeric components. Processes for preparing both block and graft copolymers in general are known in the art. Whether the copolymer useful for the microfibers herein is block or graft will depend upon the particular nature of the hydrophilizing polymeric component which is utilized in forming the copolymer.

One preferred type of hydrophilic nylon copolymer suitable for forming the essential microfiber component of the structures herein comprises the block copolymers of nylon, e.g., nylon-6, and a polyethylene oxide diamine (PEOD) component. Such copolymers can be formed by adding the PEOD component to caprolactam prior to polymerization just as any conventional terminator or stabilizer would be added. Other types of comonomers such as dicarboxylic acids, e.g. terephthalic acid, may also be added to the polymerization reaction in order to build molecular weight of the resulting copolymer. Nylon/PEOD copolymers of this type will frequently have a number average molecular weight ranging from about 5,000 to 100,000, more preferably from about 20,000 to 30,000.

The PEOD reactant used in such nylon/PEOD copolymers may itself be prepared by treating polyethylene oxide with a minimum amount of propylene oxide to generate a polyether with terminal secondary hydroxyls. Such hydroxyls can then be converted to amines to give a polyethylene glycol with amine ends. Preparation of PEOD materials of this type is described in greater detail in Yeakey; U.S. Pat. No. 3,654,370; issued Apr. 4, 1972, incorporated herein by reference. PEOD materials of this type are commercially marketed by the Jefferson Chemical Company under the trade name JEFFAMINE.

The molecular weight, melting point and melt viscosity characteristics of nylon-6/PEOD copolymer can be varied by varying the amount of PEOD incorporated into the hydrophilic nylon copolymer, by varying the molecular weight of the PEOD component itself and by varying the amount of diacid comonomer, if any, used during polymerization. Preparation of hydrophilic nylon block copolymers from nylon-6 and PEOD is described in greater detail in Lofquist et al, "Hydrophilic Nylon for Improved Apparel Comfort", *Textile Research Journal*, June 1985, pp. 325-333, which publication is incorporated herein by reference. Hydrophilic nylon block copolymers of this type are commercially marketed by Allied-Signal Inc. under the tradename HYDROFIL. Preferred hydrophilic nylon materials of this type are those wherein the copolymer contains from about 1% to 60% by weight of the PEOD component, more preferably from about 5% to 40% by weight of the PEOD component and wherein the number average molecular weight of the PEOD component itself ranges from about 100 to 10,000, more preferably from about 500 to 5,000.

Another preferred type of hydrophilic nylon copolymer suitable for forming the essential microfiber component of the absorbent structures herein comprises a graft copolymer of nylon, preferably nylon-6, and a low molecular weight poly(dimethylacrylamide) [PDMAA]. Graft copolymers of this type can be prepared by adding from about 5% to 15% by weight of reactants of a poly(N,N-dimethylacrylamide) of a certain molecular weight to from about 85% to 95% by weight of reactants of caprolactam and by then polymerizing this combination of reactants in conventional manner. The poly(N,N-dimethylacrylamide) reactant used to prepare such a graft copolymer has a molecular weight such that a 20% aqueous solution thereof has a viscosity of from about 20 to 1000 cps (0.02 to 1 Pa-s). Hydrophilic nylon graft copolymers of this type, as well as a process for their preparation, are described in greater detail in Lofquist et al; U.S. Pat. No. 4,558,097; issued Dec. 10, 1985, which patent is incorporated herein by reference.

Yet another preferred type of hydrophilic nylon copolymer suitable for forming the essential microfiber component of the absorbent structures herein comprises a block copolymer of nylon and a random poly(dioxaamide). Copolymers of this type include, for example, the copolymer prepared by polymerizing (i.e., melt blending) a mixture of caprolactam, the salt of adipic acid and 4,7-dioxadecamethylenediamine. Hydrophilic nylon copolymers of this type, as well as their preparation, are more fully described in Thompson et al; U.S. Pat. No. 4,113,754; issued Sept. 12, 1978, which patent is incorporated herein by reference. The number average molecular weight of copolymers of this type will generally range from about 5000 to 100,000.

Hydrophilic nylon copolymers having the characteristics as hereinbefore described can be melt blown into microfibers which are collected as an entangled microfiber web to form the absorbent structures of the present invention. Such webs which are fashioned entirely from microfibers of this type are especially effective at acquiring aqueous liquids such as water or aqueous body fluids and transporting such fluids through the web under the driving force of capillary pressure. While such fluid handling characteristics make webs comprised completely of hydrophilic nylon microfibers especially useful in or as absorbent structures, it will frequently be desirable to add other components to such webs in order to modify the performance properties of such webs. In some instances, it may be possible for such other components to comprise a major proportion of the web structures with the hydrophilic nylon microfiber component still providing desirable fluid management characteristics to such webs. Thus the hydrophilic nylon microfiber concentration in the web structures of the present invention can range from about 10% to 100% by weight of the structure. More preferably, the hydrophilic nylon microfiber component will comprise from about 14% to 85% by weight of the structure, most preferably from about 50% to 80% by weight of the structure.

A wide variety of optional components may be added to the hydrophilic nylon microfiber-containing webs herein to form composite absorbent structures. Such optional components include, for example, conventional relatively hydrophobic microfibers, generally larger staple fibers, non-fibrous particulate components such as polymeric gelling agent absorbents and/or fluid control particles, hydrophilizing agents, binders, perfumes, etc. Which, if any of these optional components are used depends, of course, on the particular combination of performance properties desired for the absorbent web structures of interest.

One optional component of the web structures herein which may usefully be added to such structures comprises conventional microfibers fashioned from relatively hydrophobic synthetic polymeric material. The use of microfibers of this type in absorbent structures is well known. Such conventional microfibers can be prepared from a synthetic polymer material which has a melting point of from about 100° C. to 265° C., which has an advancing contact angle with water of 90° or greater, and which will provide microfibers having a diameter of from about 1 to 50 microns. Synthetic polymer materials having such characteristics include, for example, polyolefins, polyesters, polyamides, polyacrylics and polystyrenes. Specific examples of suitable polymeric material suitable for forming conventional microfibers include polypropylene, polyethylene, polyethylene terephthalate (PET) and nylon. Polypropylene is highly preferred.

If utilized, the conventional microfiber components generally comprise no more than about 85% by weight of the web structure. Frequently in composite absorbent structures of the present invention containing conventional microfibers, the conventional microfiber component will comprise from about 10% to 50% by weight of the composite structure.

Another optional, but highly preferred, component of the hydrophilic nylon microfiber-based structures of this invention comprises natural or synthetic staple fibers. Such staple fibers will frequently be larger in diameter than microfibers. Synthetic polymeric staple fibers can have a denier ranging from about 5 to 70. More preferably the denier of synthetic polymeric staple fibers optionally employed will range between about 10 and 25.

Substantially all of the staple fibers optionally incorporated into the absorbent structures herein should range in length from about 0.1 to 15 cm, more preferably from about 2 to 7 cm. Staple fibers of these size characteristics, when combined with the hydrophilic nylon microfibers essentially utilized, serve to impart desirable bulk; improved fluid acquisition, fluid distribution and strength characteristics, and/or desirable flexibility and resilience properties to the absorbent structures of this invention.

A wide variety of staple fiber types can be employed in the absorbent structures herein. Such stable fibers include cellulosic fibers such as wood pulp fibers and modified cellulose fibers, textile fibers such as cotton or rayon and substantially nonabsorbent synthetic polymeric fibers.

For reasons of availability and cost, cellulosic fibers will frequently be preferred for use herein as an optional staple fiber component of the structures herein. Most preferred are wood pulp fibers. However, other cellulosic fiber materials may also be used. Such other cellulosic fiber materials include the stiffened, twisted, curled, cellulosic fibers which can be produced by internally crosslinking cellulose fibers with a crosslinking agent. Fibers of this general type are disclosed, for example, in Bernardin, U.S. Pat. No. 3,224,926, issued Dec. 21, 1965; Steiger, U.S. Pat. No. 3,241,553, issued Mar. 22, 1966; Chung, U.S. Pat. No. 3,440,135, issued Apr. 22, 1969; Steiger, U.S. Pat. No. 3,658,613, issued Apr. 26, 1972; Chatterjee, U.S. Pat. No. 3,932,209, issued Jan. 13, 1976 and Sangenis et al, U.S. Pat. No. 4,035,147, issued July 12, 1977, all of which patents are incorporated herein by reference.

One especially preferred type of stiffened, twisted, curled cellulose fibers useful as the optional staple fiber component of the webs herein comprises cellulose fibers which have been internally crosslinked, for example with a $C_2$–$C_8$ dialdehyde, while such fibers are in a relatively dehydrated state. Such fibers can be defined in terms of their dry fiber and wet fiber twist counts (at least 4.5 twist nodes per millimeter dry and at least 0.5 twist nodes per millimeter less than that when wet) and by their fluid retention characteristics (average isopropyl alcohol retention value of less than 30%; average water retention value of from 28% to 50%). Stiffened, curled cellulosic fibers of this preferred type are described in greater detail in Irish Patent Application No. 87-1716, filed June 26, 1987 (Available Dec. 27, 1987) and its counterpart European Patent Publication No. 252,650, published Jan. 13, 1988, both of which were filed in the name of The Procter & Gamble Company, and both of which are incorporated herein by reference.

From the standpoint of providing desirable bulk, flexibility and resiliency characteristics to the hydrophilic nylon microfiber-based absorbent structures herein, a highly preferred type of optional staple fiber comprises substantially non-absorbent, crimped synthetic polymeric fibers. The individual fibers of this type are in and of themselves substantially non-absorbent. Thus, such fibers should be prepared from synthetic polymer material which does not substantially swell or gel in the presence of fluids (e.g. urine, menses) encountered in disposable absorbent products. Accordingly, such nonabsorbent synthetic staple fibers will have a water retention value (WRV) of less than about 20%, more preferably less than about 10% and even more preferably less than 5%. The water retention value is a measure of the amount of water absorbed by the staple fibers themselves; determination of WRVs for purposes of this invention is described in greater detail hereinafter.

Suitable polymeric materials which do provide substantially nonabsorbent staple fibers of the requisite WRV include polyesters, polyolefins, polyacrylics, polyamides, polystyrenes and the like. In particular, staple fibers made of polyethylene, polypropylene and polyethylene terephthalate (PET, i.e. "Dacron") are especially preferred.

The preferred staple fibers optionally used in the absorbent structures of this invention will frequently also be crimped in order for the resulting absorbent structures to have the desired resilience and resistance to bunching during use in absorbent products. Crimped staple fibers are those which have a continuous wavy, curvy or jagged character along their length. Fiber crimping of this type is described more fully in Hauser; U.S. Pat. No. 4,118,531; issued Oct. 3, 1978, incorporated herein by reference. As noted in this '531 patent, crimped staple fibers of this type, which contribute to the desirable properties of absorbent structures containing them, are those which have a crimp count of at least two crimps per centimeter and a percent crimp of at least about 15%, preferably at least about 25%. Percent crimp is defined as the difference between the uncrimped length of the fiber (measured after fully straightening a sample fiber) and the crimped length (measured by suspending the sample fiber with a weight attached to one end equal to 2 mg. per decitex of the fiber, which straightens the large-radius bends of the fiber) divided by the crimped length and multiplied by 100.

In addition to certain absorbency and crimping characteristics, the preferred staple fibers for optional use in the structures of the present invention will also have certain stiffness characteristics. Staple fiber stiffness is a function of both fiber geometry and type of polymer material used to form the fiber. For purposes of the present invention, staple fiber stiffness can be quantified by specifying a fiber material modulus value along with fiber geometry and fiber size. The modulus of the staple fiber polymer material, e.g. the modulus of elasticity or tensile modulus, is in general defined as the ratio of change in stress to change in strain when a given amount of strain is imposed on a sample of polymeric material. Thus this modulus is usually characterized as a slope of the initial portion of the stress versus strain curve when strain is plotted as a function of applied stress for a given piece of polymeric material.

Determination of the modulus of the staple fiber polymer material can be carried out in a variety of ways on materials in fiber form as outlined in the *Handbook of Physical and Mechanical Testing for Paper and Paperboard*, Vol. 1; Richard E. Mark, Editor; Marcel Dekker, Inc.; 1983, pp 447-456 and p 465, incorporated herein by reference. Measurements of imposed strain and the resulting stress response can be carried out using, for example, Instron or Dynamic Mechanical Analyzer apparatus. Modulus determinations do not need to be carried out on materials which are actually in fiber form. Indeed, direct measurement of modulus by testing of individual staple fibers is not necessary. Instead, modulus values can and frequently are determined by testing polymeric materials in any convenient configuration, e.g. fibers, strips, pellets, etc.

The staple fiber material used in the preferred structures of the present invention should generally have a modulus value of at least about $0.1 \times 10^{10}$ dynes/cm$^2$, more preferably from about $2.5 \times 10^{10}$ to $3.5 \times 10^{10}$ dynes/cm$^2$. Since the preferred staple fibers are substantially nonabsorbent, there should be little significant difference in modulus of the staple fiber material whether the staple fiber material is wet or dry when the modulus is determined. Accordingly, the modulus value, both wet and dry, should fall within the ranges hereinbefore set forth for the preferred staple fiber material. Furthermore, the modulus value of the dry staple fiber material should not significantly diminish when the staple fiber material is wetted.

If utilized, the staple fiber component should generally comprise no more than about 90% by weight of the web structures herein. Frequently in composite absorbent structures, the staple fiber component will comprise from about 10% to 85% by weight of the composite structure, more preferably from about 20% to 50%, by weight of the composite structure.

Another optional, but highly preferred, component of the hydrophilic nylon microfiber-based absorbent structures of this invention comprises fibrous or nonfibrous particles of a specific type of hydrogel-forming polymeric gelling agent. These polymeric gelling agents are those materials which, upon contact with fluids (i.e. liquids) such as water or body fluids, imbibe such fluids and thereby form hydrogels. In this manner, fluid discharged into the absorbent structures herein can be acquired and held by the particles of the polymeric gelling agent, thereby providing the structures herein with improved absorbency characteristics.

The polymeric gelling agent particles which may be used in the hydrophilic nylon microfiber-based structures herein will generally comprise a substantially water-insoluble, slightly cross-linked, partially neutralized, hydrogel-forming polymer material. Such polymer materials can be prepared from polymerizable, unsaturated, acid-containing monomers. Thus, such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids and mixtures thereof.

Suitable unsaturated acidic monomers for use in preparing the polymeric gelling agents useful in this invention include those listed in Brandt/Goldman/Inglin; U.S. Pat. No. 4,654,039, issued Mar. 31, 1987, incorporated herein by reference. Preferred monomers include acrylic acid, methacrylic acid, and 2-acrylamido-2-methyl propane sulfonic acid. Acrylic acid itself is especially preferred for preparation of the polymeric gelling agent material.

In the hydrogel-forming polymeric gelling agents optionally used in the absorbent structures herein, the polymeric component formed from unsaturated, acid-containing monomers may be grafted on to other types of polymer moieties such as starch or cellulose. Acrylic acid grafted starch materials of this type are especially preferred for use herein.

Preferred polymer gelling agents which can be prepared from conventional types of monomers include hydrolyzed acrylonitrile grafted starch, acrylic acid grafted starch, polyacrylates, maleic anhydride-based copolymers and combinations thereof. Especially preferred are the polyacrylates and acrylic acid grafted starch.

Whatever the nature of the basic polymer components of the hydrogel-forming polymeric gelling agents optionally used in the structures herein, such materials will in general be slightly cross-linked. Cross-linking serves to render the hydrogel-forming polymer gelling agents used in this invention substantially water-insoluble, and cross-linking thus in part determines the gel volume and extractable polymer characteristics of the hydrogels formed from the polymeric gelling agents employed. Suitable cross-linking agents are well known in the art and include, for example, those described in greater detail in Masuda et al; U.S. Pat. No. 4,076,663; issued Feb. 28, 1978, incorporated herein by reference. Preferred cross-linking agents are the di- or polyesters of unsaturated mono- or polycarboxylic acids with polyols, the bisacrylamides and the di- or triallyl amines. Especially preferred cross-linking agents are N,N'-methylenebisacrylamide, trimethylol propane triacrylate and triallyl amine. The cross-linking agent can generally comprise from about 0.001 mole percent to 5 mole percent of the resulting hydrogel-forming polymer material. More preferably, the cross-linking agent will comprise from about 0.01 mole percent to 3 mole percent of the hydrogel-forming polymeric gelling agent used herein.

The slightly cross-linked, hydrogel-forming polymeric gelling agents which may be used in the fluid control system of the present invention are generally employed in their partially neutralized form. For purposes of this invention, such materials are considered partially neutralized when at least 25 mole percent, and preferably at least 50 mole percent of monomers used to form the polymer are acid group-containing monomers which have been neutralized with a salt-forming cation. Suitable salt forming cations include alkali metal, ammonium, substituted ammonium and amines. This percentage of the total monomers utilized which are neutralized acid group-containing monomers is referred to herein as the "degree of neutralization."

The polymeric gelling agent materials optionally used in the absorbent structures herein should also have a relatively high capacity for imbibing fluids encountered in absorbent structures. Absorbent capacity can be quantified by referencing the "gel volume" of the polymeric gelling agents which are to be selected for use in the absorbent structures of the present invention.

For purposes of this invention, gel volume can be defined in terms of the amount of artificial menses absorbed by any given polymeric gelling agent and is specified as grams of artificial menses per gram of polymeric gelling agent in a procedure hereinafter defined. The artificial menses used to define gel volume herein is a mixture of sheep's blood and a synthetic mucous component. The preparation of artificial menses which can be used in making gel volume determinations is set forth hereinafter in the Test Methods section.

Gel volume can be determined by swelling samples of particles of polymeric gelling agent to be tested with artificial menses fluid. Samples of polymeric gelling agent are maintained in contact with the swelling fluid at ambient temperature for about one hour so that swelling equilibrium is attained. The swollen gel samples are then centrifuged to remove fluid not actually imbibed by the polymeric gelling agent. Using a procedure described in greater detail hereinafter in the Test Methods section, the gel volume of the polymeric gelling agent in grams of artificial menses per gram of polymeric gelling agent can then be calculated from experimentally determined measurements.

The polymeric gelling agent materials useful in the absorbent structures of the present invention are those which have an equilibrium (1 hour) gel volume of at least about 20 grams of artificial menses per gram of polymeric gelling agent. More preferably, the polymeric gelling agent materials which are useful have an equilibrium (1 hour) gel volume of from about 25 to 50 grams of artificial menses per gram of polymeric gelling agent. Polymeric gelling agent material having such relatively high gel volume characteristics are especially useful in absorbent structures herein since the hydrogels formed from such materials can, by definition, hold desirably high amounts of discharged body fluids such as menses and urine.

When the absorbent structures herein are to be used in infant diapers, adult incontinence products or training pants, the gel volume of the polymeric gelling agents employed in such structures can, and frequently will, be expressed in terms of grams of synthetic urine per gram of polymeric gelling agent instead of grams of artificial menses per gram of polymeric gelling agent. Gel volume in synthetic urine can be determined by forming a suspension of about 0.1–0.2 parts of dried polymeric gelling agent to be tested with about 20 parts of this synthetic urine. This suspension is maintained at ambient temperature under gentle stirring for about 1 hour so that swelling equilibrium is attained. Using a procedure described in greater detail hereinafter in the Test Methods section, the gel volume of the polymeric gelling agent in grams of synthetic urine per gram of polymeric gelling agent is then calculated from the weight fraction of the polymeric gelling agent in the suspension and the ratio of the liquid volume excluded from the formed hydrogel to the total volume of the suspension. The structures of the present invention which are to be used in diapers, adult incontinence products or training pants will preferably employ polymeric gelling agents having a gel volume of from about 20 to 70 grams, more preferably from about 30 to 60 grams, of synthetic urine per gram of polymeric gelling agent.

Another feature of the polymeric gelling agents which are useful as an optional component of the absorbent structures herein relates to the level of extractable polymer material present in such hydrogel-forming material. Extractable polymer levels can be determined by contacting a sample of hydrogel-forming polymeric gelling agent material with a synthetic urine solution for the substantial period of time (e.g. at least 16 hours) which is needed to reach extraction equilibrium, by then filtering the formed hydrogel from the supernatant liquid, and finally by then determining the polymer content of the filtrate. Synthetic urine is utilized in such a procedure since extractable polymer content in synthetic urine is more readily determined than extractable polymer content in artificial menses. The particular procedure used to determine extractable polymer content of the polymeric gelling agents used herein is set forth in Brandt, Goldman and Inglin; U.S. Pat. No. 4,654,039; issued Mar. 31, 1987, incorporated herein by reference. Polymeric gelling agent materials especially useful in the absorbent structures herein are those which have an equilibrium extractables content in synthetic urine of no more than about 17%, preferably no more than about 10% by weight of the polymeric gelling agent.

The polymeric gelling agent materials hereinbefore described, when utilized in the absorbent structures herein, can be employed in the form of either fibrous or nonfibrous particles. Such polymeric gelling agent particles can be of any desired shape, e.g. spherical or semi-spherical, cubic, rod-like polyhedral, etc. Shapes having a large greatest dimension/smallest dimension ratio, like fibers or flakes, are also contemplated for use herein. Agglomerates of polymeric gelling agent particles may also be used.

Although the absorbent structures herein are expected to perform well with polymeric gelling agent particles having a particle size varying over a wide range, other considerations may preclude the use of very small or very large particles. For reasons of industrial hygiene, average particle sizes smaller than about 10 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Preferred for use in the fluid control systems herein are polymeric gelling agent particles substantially all of which have a particle size of from about 10 microns to about 2 mm. "Particle Size" as used herein means the smallest dimension of the individual particles.

If utilized, the polymeric gelling agent component can comprise up to about 60% by weight of the absorbent web structures herein. Frequently in composite absorbent structures, the polymeric gelling agent component will comprise from about 1% to 55% by weight, more preferably from about 5% to 50% by weight of the composite structure.

Another optional component of the hydrophilic nylon microfiber-based structures of the present invention comprises non-gelling hydrophilic particulate entities which serve to alter the fluid handling characteristics of the absorbent web structures. In particular, such hydrophilic entities facilitate the acquisition or uptake of fluid striking the surface of the web structures containing them and then serve to distribute such fluid rapidly and efficiently to more remote areas of the composite structure.

The particulate hydrophilic entities which are useful herein are those that facilitate the transport of body fluid and which may swell in doing so but which do not form gels upon imbibing such fluid. For purposes of the present invention, an entity is "hydrophilic" if, as with the hydrophilic nylon microfibers, water or aqueous body fluid readily spreads on or over the surface of the entity (without regard to whether or not the entity actually imbibes fluid or forms a gel). Furthermore, for purposes of this invention, a hydrophilic entity is non-gelling if, even upon prolonged contact with aqueous body fluids, it does not form a viscous, jelly-like material. Nongelling absorbents of this type can furthermore be characterized as those whose fluid absorbent characteristics are not dependent upon electrolyte content of the fluid being absorbed and are also less susceptible to the negative effect of body fluid solids on fluid transport. It is believed that these hydrophilic entities serve to enhance fluid transport through the absorbent structures of this invention by providing increased capillarity within the web structures. The hydrophilic particulate entities should, of course, be substantially insoluble in aqueous body fluids.

The most important feature of the nongelling hydrophilic particulate entities which may optionally be used in the absorbent structures herein is their size and geometric configuration. In particular, these entities should have a greatest dimension ranging from about 0.01 to about 10 mm, more preferably from about 0.02 to 0.5 mm. Furthermore, such entities must not have a greatest dimension to smallest dimension ratio (aspect ratio) which exceeds about 10. The aspect ratio of the hydrophilic entities will preferably be 5 or less. Particulate entities within these size and shape specifications are especially useful because entities of this particular configuration appear to significantly enhance fluid transport within and throughout composite absorbent structures herein. At the same time, entities of these size and shape specifications do not significantly interfere with the desirable resilience and flexibility characteristics of the composite absorbent structures.

Within the foregoing size and geometric shape constraints, the hydrophilic particulate entities optionally used in the absorbent structures herein can be prepared from any material which is nongelling and hydrophilic. For purposes of this invention, an entity is considered to be hydrophilic even if it has been fashioned from hydrophobic material but has been subsequently rendered hydrophilic by treatment with a hydrophilizing agent, e.g. surfactant, as hereinafter more fully described. Suitable types of hydrophilic entity material thus include cellulose, cellulose derivatives, polyolefins such as polyethylene and polypropylene, polyacrylics, polyesters, polyamides, polystyrenes, polyurethanes, clay, kaolin, talc, calcium carbonate, sodium sulfate, sodium carbonate and aluminum oxide.

Materials of the foregoing types can be fashioned into the nongelling hydrophilic particulate entities used in this invention by mechanical working to ensure that the desired size and shape parameters are met. Frequently such materials will be formed initially into fibers, flakes, sheets, films, foams, webs, etc. which will need to be chopped, torn apart, ground, powdered, twisted, knotted or otherwise finely divided in order to form particulate entities of the preferred size and geometric shape configuration.

The nongelling hydrophilic particulate entities optionally used in the absorbent structures herein may be porous or substantially nonporous. Porous, and hence relatively absorptive, hydrophilic entities are preferred. Porosity of the hydrophilic entity material may arise by virtue of the nature of the hydrophilic entity material selected or by virtue of the manner in which the hydrophilic entities are prepared.

One type of porous hydrophilic entity which may optionally be used in the web structures herein are the "fibrids" described in Parrish et al; U.S. Pat. No. 2,988,782; issued June 20, 1986, which patent is incorporated herein by reference. Those fibrids which have the size and shape characteristics set forth hereinbefore and which are or have been rendered hydrophilic can be used as the optional nongelling hydrophilic particulate entities in the absorbent structures herein.

Porous hydrophilic entities may also be prepared by fashioning the hydrophilic entities from a naturally occurring or synthetically produced porous material. Thus, materials such as foams or sponges can be employed as hydrophilic particulate entities provided such foams or sponges are finely divided into entities within the size and shape configurations hereinbefore specified. Especially preferred materials of this type include the shredded particles of hydrophilic polyurethane foam described in Isgur et al; U.S. Pat. No. 4,110,508; issued Aug. 29, 1978, incorporated herein by reference. Other preferred porous materials include finely divided particles of cellulose sponge, e.g., fine porous sponges of regenerated cellulose.

Of all the foregoing types of materials which may be used to form the optional hydrophilic particulate entity component of the absorbent structures herein, the most preferred is powdered cellulose having an average greatest dimension ranging from about 0.05 to about 0.3 mm and an average aspect ratio of 5 or less. Powdered cellulose material of this type is commercially available and is marketed, for example, under the trade name SOLKA-FLOC by the James River Corporation.

If utilized, the non-fibrous hydrophilic particulate entity component can generally comprise up to about 60% by weight of the absorbent web structures herein. Frequently in composite absorbent structures, the non-fibrous hydrophilic particulate entity component will comprise from about 1% to 50% by weight of the composite structure.

When the absorbent structures herein optionally contain two different types of non-fibrous particulate materials such as, for example, polymeric gelling agent particles and nongelling hydrophilic entity particles, these two types of particles need not be associated with each other in any specific manner other than by being incorporated into the same absorbent composite structure. On the other hand, it may be convenient to combine or premix these particle types, e.g. polymeric gelling agent and the nongelling hydrophilic particulate entities, prior to incorporating these components into the composite structures as a particulate mixture.

When polymeric gelling agent particles and nongelling hydrophilic particulate entities are both to be utilized in the structures herein, these components may also be more intimately associated than by simply being in admixture with each other. For example, gelling agents and nongelling hydrophilic entity particles may be agglomerated together so long as each type of particle in the agglomerate retains its requisite identity, size and geometric configuration. In another embodiment, polymeric gelling agent and nongelling hydrophilic entities may be associated with each other in individual particles in a core-shell arrangement with the gelling agent as the core surrounded by a nongelling hydrophilic shell.

Within the preferred composite web structures herein, the particles of optional polymeric gelling agent or hydrophobic particulate entities may or may not be uniformly distributed. In particular, there may be regions or zones of the composite web structures which have higher concentrations of such particulate components than do other regions or zones of the structure.

In one particularly preferred embodiment of this type, there may be a concentration gradient of polymeric gelling agent particles along the thickness dimension of composite absorbent structures containing such particles with the gelling agent concentration being greatest at or near the surface of the structure which does not receive the initial contact with fluid.

Yet another optional component of the hydrophilic nylon microfiber-based absorbent structures herein comprises a hydrophilizing agent which can be applied to the fibrous and non-fibrous particulate components of these structures to enhance the wettability of these fibers and particulate materials. While the use of hydrophilic nylon microfibers in the absorbent structures herein can eliminate entirely the need for a hydrophilizing agent, it still may be desirable to use such a hydrophilizing agent with some embodiments of the present invention which contain optional components made of hydrophobic materials.

Hydrophilizing agents suitable for optional use in the absorbent structures herein are well-known in the art and can comprise, for example, surfactant materials or colloidal silica. If a surfactant is employed as the hydrophilizing agent, the type of surfactant can be anionic, cationic or nonionic with nonionic materials being especially preferred. Suitable nonionic surfactants include the ethoxylated alcohols and ethoxylated alkylphenols.

The hydrophilizing agent, in either solid or liquid form, can be applied to the synthetic microfibers, staple fibers and/or non-fibrous particulate components of the absorbent structures herein at any convenient stage before, during or after preparation of such structures. Thus the hydrophilizing agent may be applied to the microfibers, staple fibers and/or non-fibrous particulates before they are comingled to form the absorbent web structures herein. Alternatively, the hydrophilizing agent may be added to the comingled mass of microfibers, staple fibers and/or non-fibrous particulate components used in forming the absorbent web structures herein. Hydrophilizing agent may furthermore be compounded with the microfiber-forming material before the microfibers are formed.

Hydrophilizing agent may also be applied to the web structures after such structures have been formed, for example, by spraying liquid nonionic surfactant onto the formed web structures. No matter how or when hydrophilizing agent is incorporated into the structures herein, if it is utilized, the hydrophilizing agent will generally comprise no more than about 10% by weight of the absorbent web structures. More preferably the amount of hydrophilizing agent will comprise from about 0.01% to 5% by weight of such structures.

The absorbent web structures of the present invention can be prepared by forming a gaseous e.g., air, stream which comprises the melt blown hydrophilic nylon microfibers, along with any other fibrous or non-fibrous optional components, and by conveying this fiber-containing or fiber/particle-containing stream to a collector device wherein an entangled mass of fibers and optionally particles is air-laid as a continuous fibrous web. Apparatus for carrying out such a process can include conventional fiber blowing structures as taught, for example, in Wente, "Superfine Thermoplastic Fibers", *Industrial Engineering Chemistry, Vol.* 48, pages 1342 et seq (1956), or in Report No. 4364 of the Naval Research Laboratories, published May 25, 1954, entitled "Manufacture of Superfine Organic Fibers" by Wente et al. These publications are incorporated herein by reference.

Typical apparatus for preparing melt blown hydrophilic nylon microfiber-based web structures of the present invention is schematically illustrated in FIG. 1 of the drawings submitted herewith. The apparatus of FIG. 1 includes a die, 10, which has an extrusion chamber, 11, through which melted, microfiber-forming, hydrophilic nylon copolymer material is advanced; die orifices, 12, arranged in line across the forward end of the die and through which the microfiber-forming, hydrophilic nylon copolymer material is extruded; and cooperating gas orifices, 13, through which a gas, typically heated air, is forced at very high velocity. The high-velocity gaseous stream draws out and attenuates the extruded microfiber-forming, hydrophilic nylon copolymer material, whereupon the microfiber-forming, hydrophilic nylon copolymer material solidifies as microfibers during travel through region, 14, to a collector, 15. The collector, 15, is typically a finely perforated screen, which in this case is in the form of a closed-loop belt, but which can take alternative forms, such as a flat screen or a drum or cylinder. Gas-withdrawal apparatus may be positioned behind the screen to assist in deposition of fibers and removal of gas. Alternatively, two dies may be used and arranged so that the streams of melt blown microfibers issuing from them intersect to form one stream that continues to a collector, 15. If desired, conventional microfibers of relatively hydrophobic material, e.g. polypropylene, can be extruded from one of the dies while hydrophilic nylon copolymer can be extruded from the other.

The apparatus shown in FIG. 1 also includes means for introducing optional non-fibrous particles and/or staple fibers into the absorbent structures of the present invention. The staple fibers can be introduced into the stream of melt blown hydrophilic nylon microfibers through the use of a lickering roll, 16. A web, 17, of crimped fibers, typically drylap or a loose, nonwoven web such as prepared on a garnet machine or "Rando-Webber", is supplied from a supply roll, 18, under a drive roll, 19, where the leading edge engages against the lickerin roll, 16. The lickerin roll, 16, turns in the direction of the arrow and picks the staple fibers from the leading edge of the web, 17, dissociating the staple fibers from one another. Optional non-fibrous particulate components can be supplied from a particle hopper, 20, containing, for example, polymeric gelling agent particles. Alternatively, separate particle hoppers (not shown) may be used to supply separate types of non-fibrous particles to the process at different rates or in different amounts. Particles from hopper, 20, are supplied through an inductor, 21, which meters the amount of particles flowing into a venturi, 22, which is in duct, 23. An air stream flows through duct, 23, for conveying the particles. The particles are conveyed to inclined duct, 24, where the fluidized stream of particles becomes the carrier stream for the staple fibers delivered by the lickerin roll, 16. The particles and staple fibers are conveyed in the air stream through inclined duct, 24, and into the stream of melt blown microfibers where the particles and staple fibers become mixed with the melt blown microfibers. The mixed stream of melt blown microfibers, staple fibers and particles then continues to the collector, 15, where a web of randomly intermixed and intertangled microfibers, staple fibers and particles is formed. A spray jet, 25, may optionally be used to apply a hydrophilizing agent, e.g. a surfactant, to the mixed stream of blown microfibers, particles and staple fibers prior to collection at collector, 15.

The absorbent web structures prepared using such apparatus generally comprise intermingled or entangled masses of hydrophilic nylon microfibers with staple fibers and non-fibrous particles as optional components. Such intermingled or entangled masses are preferably substantially unbonded in the sense that they are substantially free of significant amounts of fibers and particles bonded to each other by chemical or fusion bonds. Thus, preferably staple fibers and non-fibrous particles such as polymeric gelling agents should be combined with the hydrophilic nylon microfiber stream after the microfibers have solidified to the point that substantially no interfiber or particle-fiber fusion bonds will be formed. Rather, the structural integrity of the composite web structures herein can generally be maintained by the presence of mechanical or entanglement bonds throughout the structure.

Figure 2:
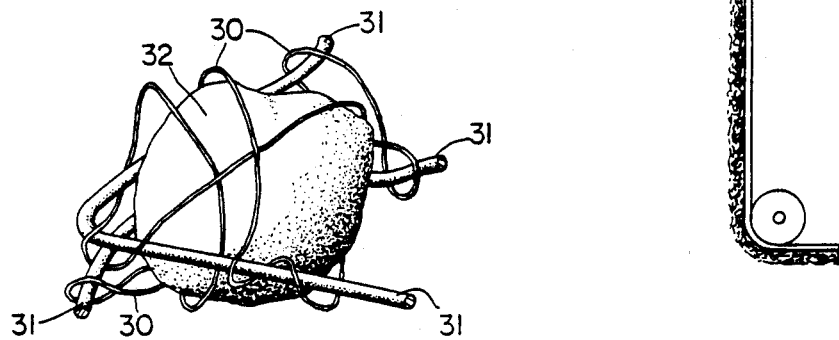
FIG. 2 is a greatly enlarged sectional representation of a portion of a preferred composite absorbent structure of this invention.

FIG. 2 of the drawing submitted herewith illustrates the general structural relationship of the microfiber, staple fiber and non-fibrous particle components in preferred composite webs of this invention. FIG. 2 shows hydrophilic nylon entangled microfibers, 30, and crimped staple fibers, 31. The microfibers in particular entangle themselves with each other, with the staple fibers and with a particle of, for example, polymeric gelling agent, 32.

The web structures of the present invention can be made having a wide variety of properties depending upon the nature and the amounts of the web components employed, upon particular fiber orientation arrangements and upon the specific processing conditions utilized. For example, the absorbent web structures herein can be prepared having any desired basis weight. For use in disposable absorbent articles, dry basis weight of the web structures herein will preferably range from about 100 to 800 g/m$^2$, more preferably from about 100 to 500 g/m$^2$. When such structures are to be used as absorbent cores for sanitary napkins, dry basis weight will generally range from about 200 to 450 g/m$^2$. When structures are to be used in infant diapers, dry basis weight will generally range from about 100 to 700 gm/m$^2$. For disposable training pants, dry basis weight will generally range from about 100 to 700 gm/m$^2$.

Caliper of the absorbent web structures herein can also be widely varied depending upon the desired end use of the structures. Frequently caliper of the dry web structure will range from about 0.46 to 3.1 centimeters, more preferably from about 1.5 to 2.1 centimeters. The preferred web structures of the present invention, by virtue of both their density and the properties of their selected types of components, do not significantly expand, i.e., increase in caliper, upon imbibing body fluids and similar electrolytes (under conditions of minimal confining pressure i.e., a confining pressure of 0.005 kPa). The preferred webs herein, in fact, may actually decrease in caliper upon fluid acquisition. These unique fluid absorption characteristics of the web structures herein may in part be responsible for the especially desirable comfort properties which preferred absorbent structures of the present invention possess.

At a constant basis weight, variations in web structure caliper result in variations in density of the structures herein. For these absorbent structures, such web density and caliper variations can influence comfort response, response to compression (i.e. bending ability and resilience), absorbent response (i.e. capacity, fluid uptake rate and fluid binding tenacity) and the ability to maintain body contact for fluid acquisition. Web density and caliper can be adjusted, for example, by varying the distance from the microfiber extruder outlet to the collector, by changing microfiber/staple fiber ratio, by altering the amount of non-fibrous particulate components employed, by changing the windup roll tension during web structure converting, by varying staple fiber denier and/or crimp level, or by calendering or compressing the web structures after they are formed. The web structures of the present invention are those which have a dry density of from about 0.006 to 0.30 g/cm$^3$, more preferably from about 0.006 to 0.15 g/cm$^3$. For use as the absorbent core in sanitary napkin products, the web structures herein should generally have a density ranging from about 0.006 to 0.10 g/cm$^3$. For use in infant diapers, the web structures herein will generally have a density ranging from about 0.01 to 0.20 gm/cm$^3$. For use in disposable training pants, density of the structures herein will generally range from about 0.01 to 0.20 gm/cm$^3$.

Dry density, for purposes of the present invention, is measured under a confining pressure of about 0.0007 psi (0.005 kPa). Density of such structures need not be uniform throughout the structure. Within the density ranges hereinbefore set forth, structures of this invention can contain regions of relatively higher or relatively lower density.

In addition to their performance in accepting and holding discharged body fluids, another important feature of the preferred composite web structures herein involves their wet and dry resilience properties. Resilience involves the propensity of the composite web structures herein to recover their original dimensions after being compressed. Preferred composite web structures of this invention are those which exhibit both wet and dry resilience properties that enable a given a three-dimensional composite web structure to recover to at least about 50%, and more preferably to at least about 65%, of its original transverse dimension after having been compressed to a transverse dimension which is 40% of its original transverse dimension. For purposes of this invention, such a determination of resilience can be made using a web structure of standard transverse dimension while embodying such a structure in a standard type of absorbent article chassis.

This standard chassis for determining web structure resilience is defined for purposes of this invention as the sanitary napkin of Example XX hereinafter set forth. The standard "original" transverse dimension utilized is 6.35 cm (2.5 inches). Thus to determine resilience of the preferred composite web structures of this invention, web structure-containing sanitary pads of a given standard initial width (2.5 inches) can be compressed to the 60% strain level, i.e., to 1.0 inch in width, (40% of its original width), followed by removal of the compressive force to allow the sanitary pad to relax. Compressive force is applied for a period of three hours, followed by a relaxation period of 5 minutes. The final width of the pad is thereafter determined. Percent Resilience can then be calculated according to the equation:

$$\% \text{ Resilience} = \left[ 1 - \frac{\text{(Initial Width} - \text{Final Width)}}{\text{Strain Level}} \right] \times 100$$

wherein Strain Level is the Initial pad width minus the Compressed Pad Width. The Percent Resilience according to this equation can be determined with the pads in either dry or wet condition.

The present invention also relates to disposable absorbent articles which utilize the absorbent structures herein as at least a portion of their fluid-absorbing "core" element. By "absorbent article" herein is meant a consumer product which is capable of absorbing significant quantities of water and other fluids (i.e., liquids), like body fluids. Examples of absorbent articles include disposable diapers, sanitary napkins, tampons, incontinence pads, disposable training pants, paper towels, facial tissues, and the like. The absorbent structures herein are particularly suitable for use in articles like sanitary napkins, diapers and incontinence pads.

Absorbent articles herein will frequently comprise a substantially liquid impervious backing sheet, a liquid pervious topsheet and an absorbent core comprising an absorbent structure of the present invention positioned between said backing sheet and said topsheet. Liquid impervious backing sheets can comprise any material, for example polyethylene or polypropylene having a caliper of about 1.5 mils, which will help retain fluid within the absorbent article. Liquid pervious top sheets can comprise any material such as polyester, polyolefin, rayon and the like which is substantially porous and permits a fluid to readily pass therethrough into the underlying absorbent core.

The absorbent core of disposable absorbent article embodiments of this invention can consist solely of one or more of the hydrophilic nylon microfiber-containing web structures herein. Alternatively, the absorbent core of such articles can comprise other conventional elements in addition to the web structures of the present invention. For example, absorbent articles herein may use a multi-layer absorbent core configuration wherein a web structure of this invention is used in combination with one or more separate layers comprising conventional absorbent structures. Such conventional absorbent structures, for example, include air-laid webs of wood pulp or other cellulosic fibers or webs of conventional melt blown microfibers. Such cellulosic or microfiber-based webs may or may not contain particles or fibers of polymeric gelling agent of the same type as hereinbefore described for use in the structures herein. Another type of conventional absorbent structure comprises a laminate of at least one layer of dispersed polymeric gelling agent particles, overwrapped with sheets of hydrophilic fiber material such as tissue paper. Laminate structures of this general type are described in Kramer, Young and Kock; U.S. Pat. No. 4,578,068; issued Mar. 25, 1986, incorporated herein by reference.

One preferred type of absorbent article herein is one which utilizes a multi-layer absorbent core having a first layer, preferably an upper layer, comprising an air-laid web of cellulosic fibers, e.g., stiffened curled cellulosic fibers, containing from 0% to about 10% by weight of this cellulosic layer of polymeric gelling agent and a second layer, preferably a lower layer, comprising a web structure of the present invention which may contain up to about 40% by weight of polymeric gelling agent. Another preferred type of absorbent article herein utilizes a multi-layer absorbent core having an upper layer comprising a web structure of the present invention and an lower layer which comprises a laminate of at least one layer of dispersed particles of polymeric gelling agent overwrapped with sheets of tissue.

For purposes of this invention, the upper layer of a multi-layer absorbent core is the layer closest to the body of the wearer, e.g. the layer closest to the article top sheet. The term lower layer conversely means the layer of a multi-layer absorbent core which is furthest away from the body of the wearer, e.g. the layer closest to the article backsheet.

As indicated hereinbefore, the fluid handling and comfort characteristics of the absorbent web structures herein render such structures especially suitable for use in absorbent articles in the form of sanitary napkins. Sanitary napkins (or in other terms, catamenial pads) utilizing the present absorbent structures may be derived from conventional sanitary napkins by simply replacing or supplementing the absorbent core thereof (typically a web of wood pulp fibers) with one or more absorbent composite structures of the present invention. In sanitary napkins, the composite structures herein may thus serve as a single layer absorbent core or may be utilized as one or more elements in a variety of multi-layered absorbent core arrangements as hereinbefore described.

Figure 3:
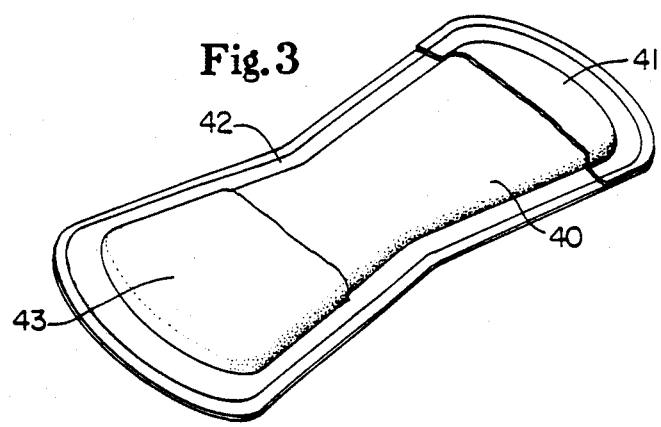
FIG. 3 represents a cut-away view of a sanitary napkin which employs an absorbent web structure of this invention as an absorbent core.

An example of a typical sanitary napkin is shown in FIG. 3 of the drawings. This particular catamenial product comprises a pad, 40, of the absorbent structure of the present invention as a single layer absorbent core; a relatively hydrophobic topsheet, 41; and a fluid impervious backsheet, 42. The topsheet and the backsheet are placed at opposite sides of the absorbent structure. Optionally, the absorbent structure is wrapped in envelope tissue, 43. Suitable materials for top sheets, bottom sheets and envelope tissue are well known in the art. A more detailed description of sanitary napkins and suitable materials for use therein is found in Duncan and Smith, U.S. Pat. No. 3,871,378, issued Mar. 18, 1975; Mullane and Smith, U.S. Pat. No. 4,324,246, issued Apr. 13, 1982 and Van Tillberg, U.S. Pat. No. 4,589,876, issued May 20, 1986; the disclosures of which are incorporated herein by reference.

Figure 4:
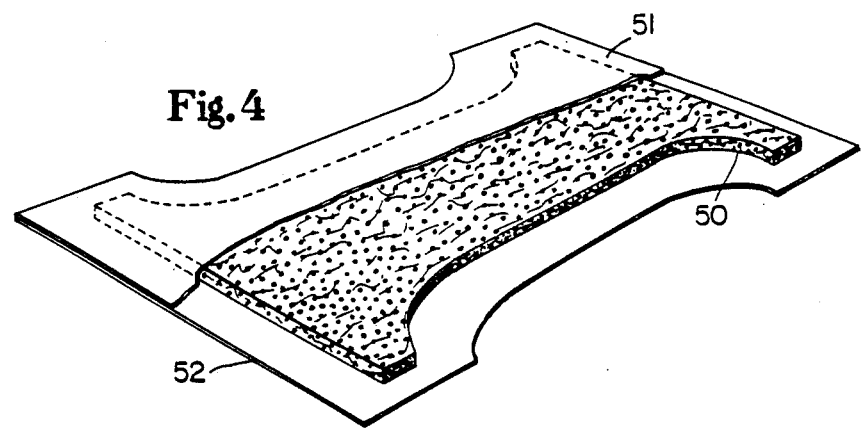
FIG. 4 represents a cut-away view of a disposable diaper which employs an absorbent web structure of this invention as an absorbent core.

Other disposable absorbent articles which can employ the absorbent web structures herein are disposable diapers. Disposable diapers comprising the absorbent structures of the present invention may be made by using conventional diaper making techniques, but by replacing or supplementing the wood pulp fiber web ("airfelt") core which is typically used in conventional diapers with one or more web structures of the present invention. Web structures of this invention may thus be used in diapers in single layer or various multiple layer core configurations. Articles in the form of disposable diapers are fully described in Duncan and Baker, U.S. Pat. No. Re. 26,151, issued Jan. 31, 1967; Duncan, U.S. Pat. No. 3,592,194, issued July 13, 1971; Duncan and Gellert, U.S. Pat. No. 3,489,148, issued Jan. 13, 1970; and Buell, U.S. Pat. No. 3,860,003, issued Jan. 14, 1975; which patents are incorporated herein by reference. A preferred disposable diaper for the purpose of this invention is illustrated by FIG. 4 of the drawings. Such a diaper includes an absorbent core, 50, comprising an absorbent structure of this invention; a topsheet, 51, superposed or co-extensive with one face of the core, and a liquid impervious backsheet, 52, superposed or coextensive with the face of the core opposite the face covered by the topsheet. The backsheet most preferably has a width greater than that of the core thereby providing side marginal portions of the backsheet which extend beyond the core. The diaper is preferably constructed in an hourglass configuration.

Another preferred type of absorbent article which can utilize the absorbent structures of the present invention comprises form fitting products such as training pants. Such form fitting articles will generally include a nonwoven, flexible substrate fashioned into a chassis in the form of briefs or shorts. An absorbent structure according to the present invention can then be affixed in the crotch area of such a chassis in order to serve as an absorbent "core." This absorbent core will frequently be over-wrapped with envelope tissue or other liquid pervious, nonwoven material. Such core overwrapping thus serves as the "topsheet" for the form fitting absorbent article.

The flexible substrate which forms the chassis of the form fitting article may comprise cloth or paper or other kinds of nonwoven substrate and may be elasticized or otherwise stretchable. Leg bands or waist bands of such training pants articles may be elasticized in conventional fashion to improve fit of the article. Such a substrate will generally be rendered liquid impervious by treating or coating one surface thereof or by laminating the flexible substrate with another liquid impervious substrate to render the total chassis liquid impervious. In this instance, the chassis itself serves as the "backsheet" for the form fitting article.

Figure 5:
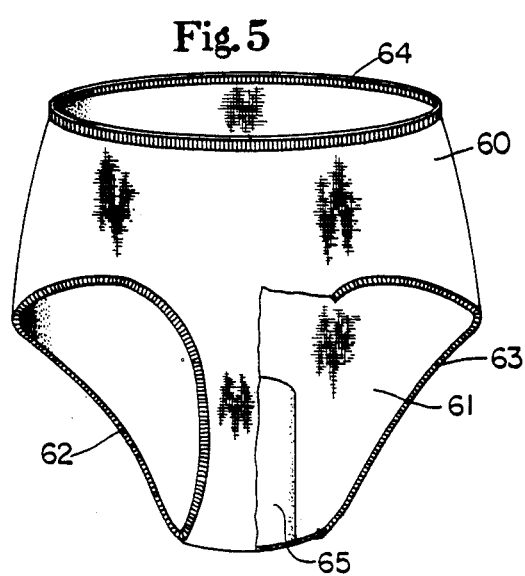
FIG. 5 represents a cut-away view of a form fitting article such as a disposable training pants product which employs an absorbent web structure of this invention as an absorbent core.

A typical form fitting article in the form of a disposable training pants product is shown in FIG. 5 of the drawing. Such a product comprises an outer layer, 60, affixed to a lining layer, 61, by adhesion along the peripheral zones thereof. For example, the inner lining, 61, may be affixed to the outer layer, 60, along the periphery of leg band area, 62; along the periphery of leg band area, 63; and along the periphery of waistband area, 64. Affixed to the crotch area of the article is a generally rectangular absorbent core, 65, comprising an absorbent structure of the present invention. Typical training pants products of this kind are described in Roberts; U.S. Pat. No. 4,619,649; issued Oct. 28, 1986, incorporated herein by reference.

TEST METHODS

In describing the present invention, characteristics of the optional, but preferred, staple fiber component such as water retention value and characteristics of the optional, but preferred, polymeric gelling agent such as gel volume are set forth. Where reported, these characteristics can be determined using the following test methods:

WATER RETENTION VALUE (WRV) OF STAPLE FIBERS

A sample of about 0.3 g to about 0.4 g of fibers is soaked in a covered container with about 100 ml distilled or deionized water at room temperature for between about 15 and about 20 hours. The soaked fibers are collected on a filter and transferred to an 80-mesh wire basket supported about 1½ inches above a 60-mesh screened bottom of a centrifuge tube. The tube is covered with a plastic cover, and the sample is centrifuged at a relative centrifuge force of 1500 to 1700 gravities for 19 to 21 minutes. The centrifuged fibers are then removed from the basket and weighed. The weighed fibers are dried to a constant weight at 105° C. and reweighed. The water retention value is calculated as follows:

$$WRV = \frac{(W - D)}{D} \times 100$$

where,
W = wet weight of the centrifuged fibers;
D = dry weight of the fibers; and
W − D = weight of absorbed water.

POLYMERIC GELLING AGENT GEL VOLUME IN ARTIFICIAL MENSES

Gel volume in artificial menses is determined as the weight (grams) of artificial menses which will be absorbed per gram of polymeric gelling agent. Such a determination is first made after two minutes of contact between gelling agent and artificial menses to give an indication of the speed with which the gelling agent takes up fluid. A determination is then made after an extended period (60 minutes) of contact between gelling agent and artificial menses in order to determine an equilibrium gel volume value.

Artificial menses employed in the gel volume comprises a mixture of sheep's blood and a synthetic mucous component. Each of these components and their preparation is described as follows:

I. ARTIFICIAL MENSES COMPONENTS

A. Mucous
  31.0 g gastric mucin (ICN Biomedicals, Inc.)
  2.0 ml prepared lactic acid solution
  7.5 ml prepared potassium hydroxide solution
  450 ml prepared phosphate buffered saline solution
B. Blood
  500 ml sterile defibrinated sheep blood (Cleveland Scientific)

II. Preparation

A. Lactic Acid Solution
  1:10 dilution of 85-95% lactic acid:distilled water
B. Potassium Hydroxide Solution
  10% (by weight) potassium hydroxide in distilled water
C. Phosphate Buffered Saline Solution
  1. Solution A:
    1.42 g anhydrous dibasic sodium phosphate
    8.50 g sodium chloride
    Add distilled water to a volume endpoint of 1 liter
  2. Solution B:
    1.38 g hydrous monobasic sodium phosphate
    8.50 g sodium chloride
    Add distilled water to a volume endpoint of 1 liter
  3. Start with 450 ml of Solution A and add Solution B to raise the pH to an endpoint of 7.2.
D. Mucous Component
  1. Combine ingredients outlined in IA.
  2. Stir (and gently heat, if necessary) to solublize.
  3. Autoclave @121° C. for 15 minutes.
  4. Let solution cool.
E. Artificial Menses Fluid
  1. Mix the mucous and blood components together.
  2. Solution must be refrigerated and brought to room temperature before using.
  3. Use within seven days due to blood aging.

Using artificial menses prepared as indicated, gel volume values are determined by a procedure wherein particles of polymeric gelling agent (PGA), held in a paper "teabag", are soaked in artificial menses fluid and are then centrifuged to remove the fluid which has not been imbibed by the PGA particles. The equipment, procedure and calculations employed in such a procedure are described as follows:

A. Equipment

Sample holders—glass cylinders (1.4 cm inside diameter, 3.4 height)

Centrifuge tubes—double chambered vessels wherein a first chamber is separated from the second chamber by a steel mesh seat for holding PGA-containing teabags Teabag material—cut to 5.0 cm X 8.0 cm rectangles Balance—0.0001 g sensitivity range Fluid bath—200 ml of swelling fluid in a 90 X 50 Pyrex crystallizing dish Centrifuge—Clinical model, with variable speed and a horizontal rotor with four 29.4 mm X 95 mm (I.D. X Depth) shields Tachometer—with adapter for measuring centrifuge speed Drying beakers—10 ml volume B. Procedure 1. Teabags are inserted into sample holders and "Initial Teabag" weights are recorded.
2. Samples of PGA are weighed out to 0.0255 g±0.0005, and "Initial PGA" weights are recorded.
3. Samples are placed in an agitated fluid bath. Liquid is pipetted over the top of the PGA to insure fluid contact and to prevent gel blockage (teabag is also completely saturated with fluid).
4. Samples are equilibrated in the bath for one hour or two minutes, depending upon which type of gel volume measurement is being made.
5. Samples are then removed from the bath. Teabags containing PGA are carefully removed from the holders and placed in the centrifuge tubes.
6. Samples are centrifuged at 125 gravities (g's) force for 10 minutes. The 10 minute time does not include the time needed for the centrifuge to reach 125 g's (1 minute, depending on the centrifuged used).
7. Samples are removed from the centrifuge tubes and weighed. The "(Wet PGA +Wet Teabag)" weights are recorded.

C. Calculations

Gel Volume can be expressed as the weight fraction of the amount of swelling fluid absorbed to the initial weight of PGA. Gel volume is defined as follows relative to experimentally measured and calculated parameters.

Gel Volume—Centrifugation

The Gel Volume Centrifugation (GVC) is calculated with the following equation:

$$GVC = \frac{Wet\ PGA - Initial\ PGA}{Initial\ PGA}$$

where the Initial PGA is the PGA sample weighed in Procedure Step #2, and the Wet PGA is the swelled PGA sample after centrifugation. The Wet PGA (WPGA) is calculated using:

$$WPGA = [(WPGA + WTB) - WTB]$$

where (WPGA+WTB) is the quantity weighed in Procedure Step #7, and WTB is the Wet Teabag. Since the wet teabag also includes some solids from the fluid, WTB is calculated using:

$$WTB = (ITB)(WTB\ factor)$$

where ITB is the Initial Teabag weight in Procedure Step #1, and the WTB factor is obtained from a calibration curve. The WTB curve for artificial menses is generated by the following equation for centrifugal force values within the ranges of 120 to 301 g's.

$$WTB\ Factor = [-0.00109 \times Centrifugal\ Force\ (g's)] + 1.85127.$$

POLYMERIC GELLING AGENT GEL VOLUME IN SYNTHETIC URINE

Gel volume in terms of grams of synthetic urine absorbed per gram of polymeric gelling agent is determined by swelling the polymer samples in several aliquots of synthetic urine. The amount of such synthetic urine actually absorbed by the polymeric gelling agent is determined by a procedure which involves use of a synthetic urine solution containing Blue Dextran so that optical absorbence measurements can be used to calculate the amount of synthetic urine that is not taken up by the hydrogel which forms.

(a) Blue Dextran Solution Preparation

A 0.03% Blue Dextran (BD) solution is prepared by dissolving 0.3 parts of Blue Dextran (Sigma D-5751) in 1000 parts of Synthetic Urine (SU) solution. Synthetic Urine is 15.0 parts of 1% TRITON X-100, 60.0 parts of NaCl, 1.8 parts of $CaCl_2 \cdot 2H_2O$, and 3.6 parts of $MgCl_2 \cdot 6H_2O$, diluted to 6000 parts with distilled $H_2O$. The resulting solution has an absorbence of about 0.25 at its absorbence maximum of 617 nm.

(b) Hydrogel Equilibration

Aliquots of the hydrogel-forming polymeric gelling agent to be tested are swelled in (i) 20 parts of Synthetic Urine (SU) solution and (ii) 20 parts of Blue Dextran (BD) solution. The suspension in the Blue Dextran (BD) solution is prepared in duplicate. For most hydrogels, 0.1–0.25 parts of hydrogel-forming dried powder is required to give a sufficiently high spectrophotometer reading relative to the Blue Dextran reference solution. One hour of equilibration at ambient temperature under gentle stir-bar stirring is sufficient for swelling equilibrium to be attained. After equilibration, a 3 ml aliquot of supernatant is separated from each gel suspension by decantation followed by centrifugation.

(c) Gel Volume Determination

The optical absorbency (ABS) of each supernatant is determined spectrophotometrically with an accuracy of 0.001 absorbence units. The Synthetic Urine solution is used as an ABS=0.0 reference. The absorbency of the supernatant from the synthetic urine suspension without Blue Dextran should not exceed 0.01 A; higher values indicate scattering from residual hydrogel gel particles or residual additives, and further centrifugation is necessary. The absorbency of the Blue Dextran supernatants should exceed the absorbency of the Blue Dextran reference solution by at least 0.1 absorbence units. Absorbency values below this range indicate the need to adjust the amount of polymeric gelling agent used to prepare the gel suspension.

(d) Gel Volume Calculation

The Gel Volume in synthetic urine of the polymeric gelling agent in gms/gm is calculated from (i) the weight fraction of the polymeric gelling agent in the gel suspension and (ii) the ratio of the excluded volume to the total volume of the suspension. Since Blue Dextran is excluded from the hydrogel due to its high molecular weight, this ratio is related to the measured absorbencies. The following equation is used to calculate the gel volume:

$$\text{Gel Volume} = \left[\frac{(\text{gms } BD \text{ Solution})}{(\text{gms polymeric gelling agent}^*)}\right] \times \left[1 - \frac{(ABS\ BD \text{ solution})}{(ABS\ BD \text{ supernatant} - ABS\ SU \text{ supernatant})}\right]$$

*Corrected to a dry weight basis

The absorbent web structures herein, as well as disposable absorbent articles containing them, are illustrated by the following examples. In these examples, reported density measurements are made under a confining pressure of 0.0007 psi (0.005 kPa) unless otherwise indicated. Furthermore ± values where reported indicate deviation at the 95% confidence level.

EXAMPLES I–XVII

A number of absorbent web structures of this invention are prepared from hydrophilic nylon microfibers. Certain of these web structures also contain crimped polyethylene terephthalate (PET) or cellulosic staple fibers, polymeric gelling agent particles, and/or particles of powdered cellulose. A more complete description of certain of these components is given as follows:

Hydrophilic Nylon Blown Microfibers (BMF)

Type = Nylon6/polyethylene Oxide Diamine (PEOD) Block Copolymer marketed by Allied-Signal Inc. under the tradename HYDROFIL
Number Average Molecular Weight = 20,000–30,000
Melting Point = 219°–224° C.
Melt Viscosity = 31 Pa-s at 265° C. and at a shear rate of 2,000 sec$^{-1}$
PEOD Molecular Weight = 2,000
Fiber Size = ranges from 1–30 microns in diameter

PET Staple Fibers

Type = KODEL PET marketed by Eastman
Size = 5, 15 or 50 denier
Water Retention Value = 5%
Percent Crimp = 40%
Fiber Material Modulus = $3.0 \times 10^{10}$ dynes/cm$^2$
Average Fiber Length = 1.5 inch (3.8 cm)

Wood Pulp Staple Fiber

Type = Foley Fluff airfelt
Size = 30 microns
Average Fiber Length = 3.5 mm.

Stiffened, Twisted, Curled Cellulosic (STCC) Staple Fiber

Type Southern softwood kraft pulp crosslinked with glutaraldehyde to the extent of 1.41 mole percent on a dry fiber cellulose anhydroglucose base
Twist Count Dry = 6.8 nodes/mm
Twist Count Wet = 5.1 nodes/mm
Isopropanol Retention Value = 24%
Water Retention Value = 37%

Polymeric Gelling Agent (PGA)

Type = Polyacrylate - AQUALIC marketed by Nippon Shokubai KK.
Size = 400 microns (mass median particle size)
Equilibrium Gel Volume (Artificial Menses) = 28.9 g/g.
Equilibrium Gel Volume (Synthetic Urine) = 30.7 g/g.

Powdered Cellulose

Type = SOLKA-FLOC KS-1016 marketed by the James River Corporation
Particle Size = 0.1 mm mean length; 0.022 mm mean diameter Aspect Ratio = 5:1

To prepare the absorbent web structures, a stream of the hydrophilic nylon microfibers is created using a die arrangement of the type shown in FIG. 1 of the drawing. The stream of hydrophilic nylon microfibers is collected as an entangled fibrous mass on a collecting drum of the general type also shown in FIG. 1. For some of the web structures of these examples, staple fibers and/or particles of polymeric gelling agent and/or powdered cellulose are also added to the hydrophilic nylon microfiber-containing stream using the lickerin roll and particulate hopper feeding apparatus as also shown in FIG. 1.

The entangled web formed on the collecting drum is removed and in some cases sections of some webs are densified to the desired density using a hydraulic press.

Using the foregoing procedure, several absorbent web structure embodiments of the present invention are prepared. These web structures vary in density and in the amount and type of optional components utilized. A description of these various web embodiments is set forth in Table I.

TABLE I

Absorbent Web Structures of Varying Density and Optional Component Content

| Example No. | Component Basis Weight (g/m²) | | | | | Web Basis Weight (g/m²) | Dry Web Density (g/cm³) | Confining Pressure for Density Measurement (psi) |
| --- | --- | --- | --- | --- | --- | --- | --- | --- |
| | BMF | Staple | PGA | Staple Type | PC | | | |
| I | 174 | — | — | — | — | 174 | 0.134 | 0.5 |
| II | 262 | — | — | — | — | 262 | 0.153 | 0.5 |
| III | 335 | — | — | — | — | 335 | 0.595 | 0.5 |
| IV | 182 | 182 | — | PET | — | 364 | 0.086 | 0.13 |
| V | 173 | 173 | — | STCC | — | 346 | 0.096 | 0.5 |
| VI | 175 | 175 | — | STCC | — | 350 | 0.268 | 0.5 |
| VII | 88 | 88 | — | STCC | — | 176 | 0.680 | 0.5 |

TABLE I-continued
Absorbent Web Structures of Varying Density and Optional Component Content

| Example No. | Component Basis Weight (g/m²) | | | | | Web Basis Weight (g/m²) | Dry Web Density (g/cm³) | Confining Pressure for Density Measurement (psi) |
|---|---|---|---|---|---|---|---|---|
| | BMF | Staple | PGA | Staple Type | PC | | | |
| VIII | 233 | — | 105 | — | — | 338 | 0.146 | 0.2 |
| IX | 208 | — | 138 | — | — | 346 | 0.152 | 0.2 |
| X | 164 | — | 165 | — | — | 329 | 0.155 | 0.2 |
| XI | 62 | 125 | 80 | PET (15 den) | — | 267 | 0.012 | 0.0007 |
| XII | 62 | 125 | 62 | PET (50 den) | — | 249 | 0.018 | 0.0007 |
| XIII | 133 | 57 | 81 | PET (5 den) | — | 271 | 0.023 | 0.0007 |
| XIV | 62 | 100 | 80 | Cotton | — | 242 | 0.012 | 0.0007 |
| XV | 62 | 125 | 80 | Rayon | — | 267 | 0.024 | 0.0007 |
| XVI | 95 | 95 | 80 | PET (15 den) | — | 270 | 0.016 | 0.0007 |
| XVII | 95 | 95 | 40 | PET (15 den) | 120 | 350 | 0.021 | 0.0007 |

The web structures described in Table I are all useful as, or as components of, absorbent cores in disposable absorbent articles of especially desirable absorbency and comfort properties. Furthermore, such structures have excellent fluid acquisition and distribution characteristics by virtue of the presence therein of the hydrophilic nylon microfiber component. Those structures containing polymeric gelling agents (Examples VIII-XVII) hold acquired body fluids in an especially tenacious manner by virtue of the fluid gelling properties of the gelling agents therein.

EXAMPLE XVIII

Absorbent properties of the hydrophilic nylon microfiber-based absorbent web structures of the present invention can be demonstrated by a zero head capillary sorption test. In such testing, samples of absorbent webs (25.52 cm²) are placed on a 6 cm diameter glass frit [Por E (ASTM 4-8 micron) from Ace Glass] and are maintained in contact with a reservoir containing synthetic urine. The height of the frit and height of the reservoir are adjusted to the same level. A confining weight of 0.5 psi is placed on top of each structure sample.

Using this setup, the number of grams of fluid taken up by the web structure as a function of time can be determined. It is also possible to calculate an initial rate of fluid uptake in grams/m²/minute. This initial rate is defined as the initial slope of the fluid uptake versus time plot, normalized over the area of contact between the sample and frit (g/m²/min). The initial slope is determined by linear regression of data points collected during the first 1.5 minutes of the capillary sorption test. If the correlation coefficient is greater than or equal to 0.98 the slope is used to calculate the initial rate. If it is not, data points are discarded until regression analysis yields a correlation coefficient that satisfies the 0.98 criterion.

Capillary sorption initial rate data for several structures of the Table I type (with some basis weight and density variations) are determined using the foregoing procedures. Also tested for capillary sorption initial rate are several comparative web structures, including several conventional structures of the prior art. These comparative web structures are described as follows:

Airfelt Webs

Webs of southern softwood pulp fibers are prepared by airlaying a stream of fibers formed by disintegrating drylap, followed by calendering or compressing of the resulting web, if necessary, to form structures of the desired density.

Stiffened, Twisted, Curled Cellulose (STCC) Webs

Webs of stiffened curled cellulose fibers similar to those of the type hereinbefore described in Examples I-XVII are prepared by airlaying a stream of these fibers. The resulting web is calendered or pressed, if necessary, to form structures of the desired density.

Polypropylene Blown Microfiber (BMF) Webs

Webs comprising blown microfibers made of polypropylene are prepared in the same general manner as are the HYDROFIL microfiber webs described in Examples I-XVII. The microfibers, however, are fashioned from polypropylene having a fiber material modulus of at least $0.9 \times 10^{10}$ dynes/cm². The polypropylene microfibers are treated with Triton GR-5M hydrophilizing surfactant at a target concentration of 1% by weight of the microfibers. These polypropylene BMF webs may also be densified by compressing swatches thereof with a hydraulic press.

ALWAYS MAXI Webs

Cores taken from a commercially marketed sanitary pad, ALWAYS MAXI, are used as comparative absorbent structures. Such cores comprise conventional airfelt webs.

Coform Webs

Cores are taken from a commercially marketed disposable incontinence brief, DEPEND, are used as comparative absorbent structures. Such cores comprise "coform" webs of melt blown polypropylene microfibers, wood pulp staple fibers and polymeric gelling agent particles. Such coform webs are in general described in Anderson et al; U.S. Pat. No. 4,100,324; Issued July 11, 1978.

Results of the capillary sorption determinations of initial rate for webs of this invention and several comparative webs are set forth in Table II.

TABLE II

| Capillary Sorption Analysis of Initial Rate - Synthetic Urine | | | |
|---|---|---|---|
| Web Type | Basis Weight (g/m²) | Dry Density (g/cm³) | Initial Rate (g/m²/min) |
| HYDROFIL BMF | 262 ± 3 | .153 ± .005 | 5210 ± 146 |
| Airfelt | 260 ± 17 | .131 ± .005 | 2679 ± 441 |
| Airfelt Pressed | 285 ± 32 | .204 ± .032 | 3576 ± 309 |
| STCC | 395 ± 17 | .067 ± .010 | 1720 ± 85 |
| STCC Pressed | 394 ± 65 | .124 ± .036 | 2003 ± 58 |
| Polypropylene BMF | 195 ± 22 | 0.090 ± 0.010 | 1602 ± 115 |
| Polypropylene BMF - Pressed | 195 ± 2 | .172 ± .035 | 2078 ± 331 |
| ALWAYS MAXI | 897 ± 81 | .078 ± .008 | 2266 ± 117 |
| Coform | 214 ± 18 | .092 ± .010 | 1331 ± 93 |

The Table II data indicate that webs containing 100% HYDROFIL BMF generate the highest capillary pressures and fastest capillary sorption rates in comparison with the other core materials listed. It is believed that this may be due to the combination of good wetting properties and small fiber size in the HYDROFIL BMF webs.

Compared to Polypropylene BMF, HYDROFIL BMF absorbs synthetic urine 2.5 times faster. Given the structural similarity of these webs, the dramatic difference in observed initial rates is hypothesized to be due to improved fluid wetting properties without surface tension reduction in the HYDROFIL BMF web.

Compared to conventional structures such as Airfelt, Coform, and STCC, the HYDROFIL BMF web also displays a significantly faster fluid sorption rate. Again, such rate differences may be primarily due to the relatively small size of the melt blown HYDROFIL fibers. This small fiber size contributes to a relatively high wettable surface area per unit of web volume, and relatively high capillary pressure is generated.

The ability of the HYDROFIL BMF web to quickly pull fluid away from a strong resistance force (i.e., the frit) suggests that the HYDROFIL BMF structure can provide uniquely positive absorptive benefits, particularly as a fluid partitioning layer in an absorbent core of a disposable absorbent article.

EXAMPLE XIX

Absorbent properties of the hydrophilic nylon microfiber-based absorbent web structures of the present invention can also be demonstrated by a certain type of horizontal gravimetric wicking (HGW) test wherein fluid uptake by the web is not impeded by the resistance force of the frit as in the capillary sorption test of Example XVIII. In the HGW testing of this example, patches of absorbent webs (25.52 cm²) are placed on a flat teflon plate, centered over a 7 mm opening. Within the opening is a glass tube (3.7 mm I.D., 6 mm O.D.) which delivers synthetic urine from a reservoir. The height of the reservoir, the top of the glass tube, and the surface of the teflon plate are all at the same level. A confining weight is placed on top of the web structure sample such that a uniform pressure of 0.5 psi (3.57 kPa) is exerted upon the sample.

Using the foregoing setup, the number of grams of fluid taken up by the web structure as a function of time can be determined. It is also possible to calculate an initial rate of fluid uptake in grams/cm²/min. As the capillary sorption test, this initial rate is defined as the initial slope of the fluid uptake versus time plot, normalized over the area of contact between the sample and the glass fluid delivery tube (0.108 cm²). The initial slope is determined by linear regression of data points collected during the first 1.0 minute of the test. If the correlation coefficient is greater than or equal to 0.98, the slope is used to calculate the initial rate. If it is not, data points are discarded until regression analysis yields a correlation coefficient that satisfies the 0.98 criterion.

Results of the HGW determination of initial rate for webs of this invention and two comparative microfiber-based webs are set forth in Table III.

TABLE III

| HGW Analysis of Initial Rate - Synthetic Urine | | | |
|---|---|---|---|
| Web Type | Basis Weight (g/m²) | Dry Density (g/cm³) | Initial Rate (g/m²/min) |
| HYDROFIL BMF | 314 ± 14 | .162 ± .006 | 14.6 ± 0.9 |
| HYDROFIL BMF Pressed | 335 ± n = 2 | .595 ± n = 2 | 2.6 ± n = 2 |
| Polypropylene BMF | 203 ± 15 | .095 ± .0003 | 7.2 ± 2.3 |
| Polypropylene BMF - Pressed | 192 ± n = 1 | .164 ± n = 1 | 1.6 ± n = 1 |

The Table III data indicate that HYDROFIL BMF webs are able to absorb synthetic urine significantly faster than conventional polypropylene webs under conditions where the fluid is in direct contact with the core material (i.e. where there is no resistance to flow imposed by the test equipment.) This difference in initial rate can be attributed to improved fluid wetting properties without surface tension reduction provided by the HYDROFIL fibers in the HYDROFIL BMF web in comparison with the polypropylene microfibers of the conventional web structure.

EXAMPLE XX

A sanitary napkin employing an absorbent structure of this invention is prepared as follows:

A hydrophilic nylon microfiber-based absorbent structure is prepared in the general manner described in Examples I–XVII, having a caliper of about 1.7 cm and a density of about 0.15 g/cm³ as measured under a confining pressure of 0.0007 psi (about 0.005 kPa). This structure is cut into a rectangular web of 7 in. × 2.5 in. (about 18 cm × 6.4 cm). This web is placed against a waterproof backing sheet (9 in. × 3 in.) of embossed polyethylene having an embossed caliper of about 2.4 mils. The web and backsheet are wrapped in a formed film polyethylene (DRI-WEAVE) having a caliper of about 17.2 mils. The web is bonded to the topsheet with a 0.001 in. film of water soluble adhesive. The ends of the resulting sanitary napkin are heat sealed and tapered. A 7 in. × 1.5 in. strip of adhesive is placed on the underside of the sanitary napkin and covered with an 8 in. × 2 in. piece of release paper. The top side of the sanitary napkin is sprayed with 0.01 g of a nonionic surfactant. The resultant absorbent article is useful as a sanitary napkin having especially desirable comfort and absorbent properties.

EXAMPLE XXI

Another form of sanitary napkin employing an absorbent structure of this invention is prepared in an hourglass-shaped configuration with "wings" and a tissue layer. To prepare such a structure, a tissue layer having an overall basis weight of 24.4 g/m² is cut in an hourglass shape such that its overall length is 8.5 inches, the center width is 3 and ⅝ inches, and the end widths are 3 and ⅞ inches. This tissue layer is bonded against a waterproof backing sheet of embossed polyethylene (having an embossed caliper of about 2.4 mils) using a ¼ inch wide strip of double-sided adhesive tape.

A hydrophilic nylon microfiber-based web structure as described in Table I, Example XVI is used as an absorbent core. Such a structure has a caliper of 1.68 cm and a density of 0.016 g/cm³ as measured under a confining pressure of 0.0007 psi. This core is cut in an hourglass shape such that its overall length is 8.25 inches, its center width is 2.2 inches, and its overall area is 20.6 square inches. This core layer is then bonded to the tissue layer using a ¼ inch wide strip of double-sided adhesive tape.

The top side of the core is then bonded to a formed film polyethylene DRI-WEAVE topsheet with a 0.001 inch film of water soluble adhesive. This layered structure is then heat sealed (seal forms between topsheet and backsheet) with the core centered. A cut is then made along the heat seal such that final product dimensions are 9.5 inches in length, 4.5 inches in width at the ends, and 7 inches in width at the center where the product wings are located. A 8.25 inch by 2 inch strip of adhesive is placed on the underside of the sanitary napkin and covered with a 9 inch by 2.25 inch piece of release paper. Adhesive pieces 1 inch by 1 inch are placed on the underside of each wing and covered with 1.25 inch by 1.25 inch pieces of release paper. The top side of the sanitary napkin is sprayed with 0.01 grams of nonionic surfactant. The resulting absorbent article is useful as a sanitary napkin having especially desirable comfort and fluid handling properties.

EXAMPLE XXII

A diaper is prepared as described in U.S. Pat. No. 3,860,003, Buell, Issued Jan. 14, 1975, incorporated herein by reference, except that, in place of the absorbent diaper core disclosed therein (e.g. made from airlaid wood pulp) there is utilized as a core inserted between the top sheet and the backsheet an hourglass-shaped web structure of the present invention. The absorbent structure is made as described in Table I, Example XVII. The gel volume of the AQUALIC PGA is approximately 30 grams of synthetic urine per gram of gelling agent. The basis weight of the structure is 350 gm/m²; the density is 0.024 gm/cm³, resulting in a core thickness of 1.46 cm, measured at a confining pressure of 0.0007 psi.

EXAMPLE XXIII

Absorbent web structures of the present invention are made with hydrophilic nylon HYDROFIL microfibers, crimped PET staple fibers, and particles of acrylic acid grafted starch hydrogel having a weight average particle size of about 25 microns (SANWET IM-1000, from Sanyo Co., Japan) using the process described in Examples I-XVII. The SANWET IM-1000 has a gel volume of approximately 48 grams of synthetic urine per gram of gelling agent. The absorbent structures have a basis weight of 270 gm/m² and a caliper of ~1.7 cm which corresponds to a density of ~0.016 gm/cm³. The structures are covered with a sheet of envelope tissue and cut to a size of 3.5 in.×15.5 in. (about 9×40 cm).

Absorbent structures of this type are then used as inserts in diaper products prepared as described in U.S. Pat. No. 3,860,003, Buell, issued Jan. 14, 1975, incorporated herein by reference. The hourglass-shaped soft wood pulp cores of the diapers have the following dimensions: length: 15.5 in. (about 40 cm), width at the ears: 10.5 in. (about 27 cm), and width in the center: 3.75 in. (about 9.5 cm). The absorbent web structures of this invention are inserted lengthwise into the above-described diapers, in between the hourglass-shaped core and the polyethylene backing sheet, the envelope tissue against the hourglass-shaped core.

Such inserts improve the absorbent capacity of these diapers for urine.

What is claimed is:

1. An absorbent structure especially suitable for acquiring and distributing aqueous fluids throughout such a structure, which structure comprises an entangled web of melt-blown microfibers having diameters which range from about 0.5 to 60 microns, said microfibers being formed from a thermoplastic copolymer comprising a nylon component and a hydrophilizing polymeric component which renders said copolymer hydrophilic and which provides a copolymer having a melting point of from about 100° C. to 265° C. and a melt viscosity of from about 1 to 400 Pa-sec.; said web having a dry density of from about 0.006 to 0.3 g/cm³.

2. An absorbent structure according to claim 1 wherein the hydrophilic nylon copolymer used to form the microfibers has a melting point of from about 200° C. to 250° C. and a melt viscosity of from about 10 to 150 Pa-s.

3. An absorbent structure according to claim 2 wherein the microfibers forming said structure range in diameter from about 1 to 30 microns and wherein said structure has a dry density of from about 0.006 to 0.15 g/cm³.

4. An absorbent structure according to claim 2 wherein the hydrophilic nylon copolymer used to form the microfibers is a block copolymer of nylon and a polyethylene oxide diamine, said block copolymer having a number average molecular weight of from about 5,000 to 100,000.

5. An absorbent structure according to claim 4 wherein the hydrophilic nylon copolymer used to form the microfiber component is a block copolymer of nylon-6 and a polyethylqne oxide diamine wherein said polyethylene oxide diamine has a number average molecular weight of from about 100 to 10,000 and comprises from about 1% to 60% by weight of the block copolymer.

6. An absorbent structure according to claim 2 wherein the hydrophilic nylon microfiber component comprises from about 14% to 85% by weight of the structure and wherein the structure also comprises an additional component selected from relatively hydrophobic microfibers, staple fibers, nonfibrous particles of polymeric gelling agent absorbent, nonfibrous fluid control particles, hydrophilizing agents and combinations of such additional components.

7. An absorbent structure according to claim 6 wherein the additional component is a staple fiber component which comprises from about 10% to 50% by weight of the structure and wherein said staple fibers are selected from wood pulp fibers; stiffened, twisted, curled, cellulosic fibers; cotton fibers; rayon fibers and substantially nonabsorbent synthetic polymeric fibers.

8. An absorbent composite structure especially suitable for use in disposable absorbent articles of improved comfort, wet integrity and fluid handling characteristics, said composite structure comprising (A) from about 14% to 85% by weight of the composite of hydrophilic nylon melt blown microfibers, substantially all of which are of a diameter of from about 0.5 to 60 microns, said microfibers being formed from a thermoplastic copolymer comprising a nylon component and a hydrophilizing polymeric component which renders said copolymer hydrophilic and which provides a copolymer having a melting point of from about 100° C. to 265° C. and a melt viscosity of from about 1 to 400 Pa-sec.;

(B) from about 10% to 85% by weight of the composite of substantially nonabsorbent synthetic staple fibers, substantially all of which have a denier of from about 5 to 70 and a percent crimp of at least about 15%, said staple fibers being formed from a synthetic polymeric material having a modulus value when dry of at least about $0.1 \times 10^{10}$ dynes/cm$^2$, said modulus value not diminishing significantly when said staple fibers are wet; and (C) from about 1% to 55% by weight of the composite of nonfibrous particles of a hydrogel-forming polymeric gelling agent having an equilibrium gel volume of at least about 20 grams of synthetic urine or artificial menses per gram of gelling agent, substantially all of said polymeric gelling agent particles ranging in diameter from about 10 microns to 2 mm;

said hydrophilic nylon melt blown microfibers, staple fibers and polymeric gelling agent particles being combined in a manner which forms a composite web having a dry density of from about 0.006 to 0.3 g/cm$^3$.

9. An absorbent composite structure according to claim 8 wherein
   (A) the hydrophilic nylon copolymer used to form the microfibers has a melting point of from about 200° C. to 250° C. and a melt viscosity of from about 10 to 150 Pa-s;
   (B) the substantially nonabsorbent crimped synthetic staple fibers are formed from a synthetic polymeric material selected from polyolefins, polyesters, polyacrylics; polyamides and polystyrenes; and
   (C) the polymeric gelling agent is selected from hydrolyzed acrylonitrile grafted starch, acrylic acid grafted starch, polyacrylates, maleic anhydride-based copolymers and combinations thereof.

10. An absorbent composite according to claim 9 wherein
   (A) the hydrophilic nylon copolymer used to form the microfiber compound is a block copolymer of nylon and a polyethylene oxide diamine, said block copolymer having a number average molecular weight of from about 5,000 to 100,000;
   (B) the staple fibers utilized are polyethylene terephthalate staple fibers, substantially all of which have a denier of from about 10 to 25 and a fiber length between about 1.0 and 15 cm; and
   (C) the polymeric gelling agent utilized is selected from slightly cross-linked, partially neutralized polyacrylates and acrylic acid grafted starch, has an equilibrium gel volume of at least about 20 grams of synthetic urine or artificial menses per gram of polymeric gelling agent and has an extractable polymer content in synthetic urine of no more than about 17% by weight.

11. An absorbent composite structure according to claim 10 wherein the hydrophilic nylon copolymer used to form the microfiber component is a block copolymer of nylon-6 and a polyethylene oxide diamine wherein said polyethylene oxide diamine has a number average molecular weight of from about 100 to 10,000 and comprises from about 1% to 60% by weight of the block copolymer and wherein the absorbent composite structure has a density of from about 0.006 to 0.15 g/cm$^3$.

12. An absorbent article of improved comfort, wet integrity and fluid handling characteristics, said article comprising:
   (A) a liquid impervious backing sheet;
   (B) a liquid pervious topsheet; and
   (C) an absorbent core positioned between said backing sheet and said topsheet, said absorbent core containing an absorbent structure which comprises an entangled web of melt-blown microfibers having diameters which range from about 0.5 to 60 microns, said microfibers being formed from a thermoplastic copolymer comprising a nylon component and a hydrophilizing polymeric component which renders said copolymer hydrophilic and which provides a copolymer having a melting point of from about 100° C. to 265° C. and a melt viscosity of from about 1 to 400 Pa-sec.; said web having a dry density of from about 0.006 to 0.3 g/cm$^3$.

13. An absorbent article according to claim 12 wherein
   (A) the hydrophilic nylon copolymer used to form the microfibers of the absorbent structure component of the absorbent core is a block copolymer of nylon and a polyethylene oxide diamine, said block copolymer having a number average molecular weight of from about 5,000 to 100,000;
   (B) the microfibers of the absorbent structure component of the absorbent core range in diameter from about 1 to 30 microns; and
   (C) the absorbent structure component of the absorbent core has a dry density of from about 0.006 to 0.15 g/cm$^3$.

14. An absorbent article according to claim 13 wherein the absorbent structure component of the absorbent core comprises from about 14% to 85% by weight of the structure of microfibers and wherein the structure also comprises an additional component selected from cellulosic staple fibers, substantially nonabsorbent synthetic polymeric staple fibers, particles of polymeric gelling agent absorbent and combinations of such additional components.

15. An absorbent article according to claim 14 wherein the absorbent structure component of the absorbent core contains cellulosic staple fibers selected from wood pulp fibers and stiffened, twisted, curled cellulosic fibers.

16. An absorbent article according to claim 14 wherein the absorbent structure component of the absorbent core contains
   (A) from about 10% to 85% by weight of the structure of substantially nonabsorbent crimped synthetic staple fibers, substantially all of which have a denier of from about 10 to 25, and a percent crimp of at least about 15%, said staple fibers being formed from synthetic polymeric material selected from polyolefins, polyesters, polyacrylics, polyamides and polystyrenes; and
   (B) from about 1% to 55% by weight of the structure of nonfibrous particles of a hydrogel-forming polymeric gelling agent having an equilibrium gel volume of at least about 20 grams of synthetic urine or artificial menses per gram of gelling agent and an extractable polymer content in synthetic urine of no more than about 17% by weight, substantially all of said polymeric gelling agent particles ranging in diameter from about 30 microns to 2 mm.

17. An absorbent article according to claim 13 in the form of a disposable diaper wherein (A) said topsheet is coextensive with one face of said absorbent core;
(B) said backing sheet is coextensive with the face of the core opposite the face covered by said topsheet and has a width greater than that of the core, to thereby provide side marginal portions of the backing sheet which extend beyond the core; and
(C) said absorbent core is hourglass-shaped.

* * * * *